US007943753B2

(12) United States Patent
Orozco, Jr. et al.

(10) Patent No.: US 7,943,753 B2
(45) Date of Patent: May 17, 2011

(54) AUXIN TRANSPORT PROTEINS

(75) Inventors: Emil M. Orozco, Jr., Cochranville, PA (US); Rebecca E. Cahoon, Lincoln, NE (US); Wesley B. Bruce, Raleigh, NC (US); Yong Tao, Newark, DE (US); Zude Weng, Rolling Meadows, IL (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 56 days.

(21) Appl. No.: 12/620,840

(22) Filed: Nov. 18, 2009

(65) Prior Publication Data

US 2010/0077505 A1 Mar. 25, 2010

Related U.S. Application Data

(60) Division of application No. 12/173,868, filed on Jul. 16, 2008, now Pat. No. 7,638,681, which is a division of application No. 10/987,855, filed on Nov. 12, 2004, now Pat. No. 7,422,901, which is a continuation of application No. 10/030,884, filed as application No. PCT/US00/12061 on May 3, 2000, now abandoned.

(60) Provisional application No. 60/133,040, filed on May 7, 1999.

(51) Int. Cl.
*C12N 15/29* (2006.01)
(52) U.S. Cl. ..................................... 536/23.6
(58) Field of Classification Search .......... None
See application file for complete search history.

(56) References Cited

U.S. PATENT DOCUMENTS

| 4,945,050 A | 7/1990 | Sanford et al. |
| 2004/0216190 A1 | 10/2004 | Kovalic |

FOREIGN PATENT DOCUMENTS

| EP | 0 242 236 B2 | 8/1996 |
| EP | 0 814 161 A1 | 12/1997 |
| WO | 99/63092 A1 | 12/1999 |

OTHER PUBLICATIONS

Bowie et al, Science 247:1306-1310, 1990.*
McConnell et al, Nature 411 (6838):709-713, 2001.*
Benjamins et al (2001, Development 128:4057-4067).*
National Center for Biotechnology Information General Identifier No. 7489524, Accession No. T02876, Jul. 21, 2000, C. Luschnig et al., EIR1, A Root-Specific Protein Involved in Auxin Transport, is Required for Gravitropism in *Arabidopis thaliana*.
C. Luschnig et al., Genes and Development, vol. 25, No. 14:2175-2187, 1998, EIR1, A Root Specific Protein Involved in Auxin Transport, is Required for Gravitropism in *Arabidopsis thaliana*, XP002116368.
National Center for Biotechnology Information General Identifier No. 5902405, Accession No. AAD55507, Sep. 16, 1999, N. A. Federspiel et al.
National Center for Biotechnology Information General Identifier No. 5817301, Accession No. AAD52695, Sep. 2, 1999, J. Friml et al.
Rujin Chen et al., PNAS, vol. 95:15112-15117, 1998, The *Arabidopsis thaliana* Agravitropic 1 Gene Encodes a Componet of the Polar-Ayxin-Transport Efflux Carrier.
Desmond G. Higgins et al., Cabios Comm., vol. 5:151-153, 1989, Fast and Sensitive Multiple Sequence Alignments on a Microcomputer.
Chu Chih-Ching et al., Sci. Sin. Peking, vol. 18:659-668, 1975, Establishment of an Efficient Medium for Anther Culture of Rice Through Comparative Experiments on the Nitrogen Soruces.
Stephen F. Altschul et al., J. Mol. Biol., vol. 215:403-410, 1990, Basic Local Alignment Search Tool.
Warren Gish et al., Nature Genetics, vol. 3:266-272, 1993, Identification of Protein Coding Regions by Database Similarity Search.
Mark D. Adams et al., Science, vol. 252:1651-1656, 1991, Complementary DNA Sequencing: Expressed Sequence Tags and Human Genome Project.
T. M. Klein et al., Nature, vol. 327:70-73, 1987, High-Velocity Microprojectiles for Delivering Nucleic Acids Into Living Cells.
Joan T. Odell et al., Nature, vol. 313:810-812, 1985, Identification of DNA Sequences Required for Activity of the Cauliflower Mosaic Virus 35S Promoter.
EMBL Sequence Database Library Accession No. 081215, Nov. 1, 1998, C. Lusching et al. EIR1, A Root-Specific Protein Involved in Auxin Transport, is Required for Gravitropism in *Arabidopis thaliana*.
Etienne Schwob et al., Plant J., vol. 4:423-432, 1993, Molecular Analysis of Three Maize 22 KDA Auxin-Binding Protein Genes—Transient Promoter Expression and Regulatory Regions.
Rolf Zettl et al., PNAS, vol. 89:480-484, 1992, 5'-Azido-[3,6-3H2]-1-Naphthylphthalamic Acid, A Photoactivatable Probe for Naphthylphthalamic Acid Receptor Proteins From Higher Plants: Identification of a 23-KDA Protein From Maize Coleoptile Plasma Membranes.
Leo Galweiler et al., Science, vol. 282:2226-2230, 1998, Regulation of Polar Auxin Transport by ATPIN1 in *Arabidopsis* Vascular Tissue.
Malcolm J. Bennett et al., Science, vol. 273:948-950, 1996, *Arabidopsis* AUX1 Gene: A Permease-Like Regulator of Root Gravitropism.
National Center for Biotechnology Information General Identifier No. 3377509, Access No. AAC39514, Aug. 3, 1998, C. Luschnog et al., EIR1, A Root-Specific Protein Involved in Auxin Transport, is Required From Gravitropism in *Arabidopsis thaliana*.
National Center for Biotechnology Information General Identifier No. 3377507, Accession No. AAC39513, Aug. 3, 1998, C. Luschnig et al., EIR1, A Root-Specific Protein Involved in Auxin Transport, is Required for Gravitropism in *Arabidopsis thaliana*.

(Continued)

*Primary Examiner* — Stuart F. Baum

(57) ABSTRACT

This invention relates to an isolated nucleic acid fragment encoding an auxin transport protein. The invention also relates to the construction of a chimeric gene encoding all or a substantial portion of the auxin transport protein, in sense or antisense orientation, wherein expression of the chimeric gene results in production of altered levels of the auxin transport protein in a transformed host cell. The present invention also relates to methods using the auxin transport protein in modulating root development, and in discovering compounds with potential herbicidal activity.

1 Claim, 4 Drawing Sheets

OTHER PUBLICATIONS

National Center for Biotechnology Information General Identifier No. 4151319, Accession No. AAD04376, Jan. 13, 1999, L. Galweiler et al., Regulation of Polar Auxin Transport by ATPIN1 in *Arabidopsis* Vascular Tissue.

National Center for Biotechnology Information General Identifier No. 3785972, Accession No. AAC67319, Apr. 5, 2000, X. Lin et al., Sequence and Analysis of Chromosome 2 of the Plant *Arabidopsis thaliana*.

X. Lin et al., Nature, vol. 402:761-768, 1999, Sequence and Analysis of Chromosome 2 of the Plant *Arabidopsis thaliana*.

Michael E. Fromm et al., Biotech., vol. 8:833-839, 1990, Inheritance and Expression of Chimeric Genes in the Progeny of Transgenic Maize Plants.

Jeff J. Doyle et al., Journal of Biol. Chem., vol. 261:9228-9238, 1986, The Glycosylated Seed Storage Proteins of *Glycine max* and *Phaseolus vulgaris*.

Linda Gritz et al., Gene, vol. 25:179-188, 1983, Plasmid-Encoded Hygromycin B Resistance the Sequence of Hygromycin B Phosphotransferase Gene and Its Expression in *Escherichia coli* and *Saccharomyces cerevisiae*.

Alan H. Rosenberg et al., Gene, vol. 56:125-135, 1987, Vectors for Selective Expression of Cloned DNAs by T7 RNA Polymerase.

F. William Studiee et al., J. Mol. Biol., vol. 189:113-130, 1986, Use of Bacteriophage T7 RNA Polymerase to Direct Selective High-Level Expression of Cloned Genes.

N. Carraro et al., ZmPIN1a and ZmPIN1b Encode Two Novel Putative Candidates for Polar Auxin Transport and Plant Architecture Determination of Maize, Plant Physiol., vol. 142:254-264, Sep. 7, 2006, Accession No. ABH09242.

N. Carraro et al., ZmPIN1a and ZmPIN1b Encode Two Novel Putative Candidates for Polar Auxin Transport and Plant Architecture Determination of Maize, Plant Physiol., vol. 142:254-264, Sep. 7, 2006, Accession No. ABH09243.

Xu Min et al., A PIN1 Family Gene, OsPIN1, Involved in Auxin-Dependent, Plant Cell Physiol., vol. 46:1674-1681, 2005.

National Center for Biotechnology Information General Identifier No. 20197401, Accession No. AAC67319, Mar. 11, 2002, S. D. Roundsley et al., Putative Auxin Transport Protein (*Arabidopsis thaliana*).

Bowie et al., Science, vol. 247:1306-1310, 1990.

Kano-Murakami et al., FEBS, 1993, vol. 334:365-368.

Benjamins et al., Development, 2001, vol. 128:4057-4067.

McConnell et al., Nature, vol. 411:709-713, 2001.

Carraro, Nicola et al., "ZmPIN1a and ZmPIN1b Encode Two Novel Putative Candidates . . . ", Plant Physiology, Sep. 2006, vol. 142, pp. 254-264.

National Center for Biotechnology Information General Identifier No. 6482022, Accession No. AW201293, Dec. 1, 1999, Shoemaker et al., sf01c09.y1 Gm-c1027 *Glycine max* cDNA clone Genome Systems Clone ID: Gm-c1027-1001 5' similar to TR:Q9ZSY5 Q9ZSY5 Putative Auxin Efflux Carrier Protein; mRNA sequence.

Loper et al., Auxin Transport in Suspension-Cultured Soybean Root Cells I. Characterization, Plant Physiology (Rockville), 1991, p. 184-191, vol. 96(1).

Loper et al., Auxin Transport in Suspension-Cultured Soybean Root Cells II. Anion Effects on Carrier-Mediated Uptake, Plant Physiology (Rockville), 1991, p. 192-197, vol. 96(1).

Nelson et al., Expressed Sequences From Conidial, Mycelial, and Sexual Stages of *Neurospora crassa*, Fungal Genetics and Biology, 1997, p. 348-363, vol. 21(3).

\* cited by examiner

```
SEQ ID NO:14    MITALDLYHVLTAVVPLYVAMTLAYGSVRWRIETPDQCSGINRFVALFAVPLLSFHFIS
SEQ ID NO:30    MITLTDFYHVMTAMVPLYVAMILAYGSVKWWKIFSPDQCSGINRFVALFAVPLLSFHFIA
SEQ ID NO:34    MITGKDIYDVFAAIVPLYVAMILAYGSVRWWKIFTPDQCSGINRFVAVFAVPLLSFHFIS
SEQ ID NO:38    MITGKDIYDVLAAVVPLYVAMFMAYGSVRWWGIFTPDQCSGINRFVAVFAVPLLSFHFIS
SEQ ID NO:43    MITGKDMYDVLAAMVPLYVAMILAYGSVRWWGIFTPDQCSGINRFVAVFAVPLLSFHFIS
SEQ ID NO:44    MITAADFYHVMTAMVPLYVAMILAYGSVKWWKIFTPDQCSGINRFVALFAVPLLSFHFIA
                1                                                           60

SEQ ID NO:14    TNDPFAMNLRFLAADTLQKVAVLALLALASRGLSSPRALG------LDWSITLFSLS
SEQ ID NO:30    SNNPYEMNLRFLAADTLQKIIILVLLAVW----SNITKRG------CLEWAITLFSLS
SEQ ID NO:34    SNDPYAMNYHFIAADCLQKVVILGALFLWNT----FTKHG------SLDWTITLFSLS
SEQ ID NO:38    TNDPYAMDYRFLAADSLQKLVILAALAVWHNVLSRYRCRGGTEAGEASSLDWTITLFSLA
SEQ ID NO:43    SNDPYAMNYHFLAADSLQKVVILAALFLWQA----FSRRG------SLEWMITLFSLS
SEQ ID NO:44    ANNPYAMNLRFLAADSLQKVIVLSLLFLW----CKLSRNG------SLDWTITLFSLS
                61                                                          120

SEQ ID NO:14    TLPNTLVMGIPLLRGMYGASSAGTLMVQVVLQCIIWYTLMLFLFEYRAARALVLDQFPD
SEQ ID NO:30    TLPNTLVMGIPLLKGMYGDFS-GSLMVQIVVLQCIIWYTLMLFLFEFRGARMLISEQFP-
SEQ ID NO:34    TLPNTLVMGIPLLKAMYGDFS-GSLMVQIVVLQSVIWYTLMLFLFEYRGAKLLITEQFP-
SEQ ID NO:38    TLPNTLVMGIPLLRAMYGDFS-GSLMVQIVVLQSVIWYTLMLFMFEYRGAKALISEQFPP
SEQ ID NO:43    TLPNTLVMGIPLLRRAMYGDFS-GNLMVQIVVLQSIIWYTLMLFEFERGAKLLISEQFP-
SEQ ID NO:44    TLPNTLVMGIPLLKGMYGNFS-GDLMVQIVVLQCIIWYILMLFLFEYRGAKLLISEQFP-
                121                                                         180
```

FIG. 1A

```
SEQ ID NO:14    GAAASIVSFRVDSDVVSLARGDVELEAEPDGVAGAGAVSSRGGDAGRVRTVTVRKSTSSRS
SEQ ID NO:30    DTAASIVSIHVDSDVVSLN-GREPLQTDAEI--------------KEDGKLHVTVRKSNASRS
SEQ ID NO:34    ETAGSITSFRVDSDVVSLN-GREPLQTDAEI--------------GEDGKLHVVVKRS-AASS
SEQ ID NO:38    DVGASIASFRVDSDVVSLN-GREALHADAEV--------------GRDGRVHVVIRRSASGST
SEQ ID NO:43    ETAGSITSFRVDSDVISLN-GREPLQTDAEI--------------GDDGKLHVVVRRSSAASS
SEQ ID NO:44    DTAGSIVSIHVDSDIMSLD-GRQPLETEAEI--------------KEDGKLHVTVRRSNASRS
                                                                            240

SEQ ID NO:14    EAACSHSHSQ-------TMQPRVSNLSGVEIYSLQSSRNPTPRGSSFNHADFFNIVGAA-
SEQ ID NO:30    DI---FSRR---SQGLSSTTPRPSNLTNAEIYSLQSSRNPTPRGSSFNHTDFYSMMAAG-
SEQ ID NO:34    MIS-SFNKSHLTSM------TPRASNLTGVEIYSVQSSREPTPRGSSFNQTDFYAMF-ASK
SEQ ID NO:38    TGGHGAGRSGIYRGASNAMTPRASNLTGVEIYSLQTSREPTPRQSSFNQSDFYSMFNGSK
SEQ ID NO:43    MIS-SFNKSHGGLNSSMITPRASNLTGVEIYSVQSSREPTPRASSFNQTDFYAMFNASK
SEQ ID NO:44    DI---YSRR---SQGLSAT-PRPSNLTNAEIYSLQSSRNPTPRGSSFNHTDFYSMMASG-
                                                                            300

SEQ ID NO:14    ---AKGG------------GGAAGDE---------------------------------
SEQ ID NO:30    -----G-RNSNF----GASD-VYGLSASRGPTPRPSNYDEDGGKP--K-------------
SEQ ID NO:34    APSPKHGYTNSFQSNNGGIG-DVYSLQSSKGATPRTSNFEEEMLKMHKK--RGGRSMSGE
SEQ ID NO:38    LASPKG------QPPVAGGGG--------ARGQGLDEQVANK-----------------
SEQ ID NO:43    APSPRHGYTNSYGGAGAGPGGDVYSLQSSKGVTPRTSNFDEEVMKTAKKAGRGGRSMSGE
SEQ ID NO:44    -----GGRNSNF-----GPGEAVFG---SKGPTPRPSNYEEDGGPA--KPTAAGTAAGAG
                                                                            360
```

FIG. 1B

```
                                *                                                       *    *    *                                                                *
SEQ ID NO:14    ----EKGACGGGGGGHSPQPQA------------------------------VAVPAKRKDLHM
SEQ ID NO:30    -FHYHA-----AGGTGHYPAPNPGMFSPSNGSKSVAANANAKRPNGQAQLKPEDGNRDLHM
SEQ ID NO:34    LFN--------GGLVSSNYPPPNP-MFSGSTSAAGGPKKKDSSGGG-----GAVAPNKELHM
SEQ ID NO:38    -FK--------GEAAAPYPAPNP-GMM-------MPAPRKKELGGSNSNS-------DKELHM
SEQ ID NO:43    LYN-------NNSVPS-YPPPNP-MFTGSTSGASGVKKKESGGGGSGGGGVGGQNKEMNM
SEQ ID NO:44    RFHYQSGGGSGGGGAHYPAPNPGMFSPNTGGGGGTAAKGNAPVVGGK--RQDGNGRDLHM
                                                                                                                                      420

*********                                                             *        *
SEQ ID NO:14    LVWSSSASPVSE-------RAAVHVFGAGGA-----DHADVLAKGAQAYDEY---GRDDY
SEQ ID NO:30    FVWSSSASPVSDV------------------FGA------HEYGGG--HDQKEVKLNVSPGKVEN
SEQ ID NO:34    FVWSSSASPVSEGNLRHAVNRAASTDFGTVDPSKAVPHETVASKAVHELIENMSPGRRGS
SEQ ID NO:38    FVWSSSASPVSEANLRNAVNHAASTDFEAAAPPAAATPRDGATPRGVSGSVTPVMKKDASS
SEQ ID NO:43    FVWSSSASPVSEANAKNAMTRGSSTDVSTDPKVSIPPHDNLATKAMQNLIENMSPGRKGH
SEQ ID NO:44    FVWSSSASPVSDV-------------------FGGGGGNHHADYSTATNDHQKDVKISVPQGNSND
                                                                                                                                      480

*** ********
SEQ ID NO:14    SSRTKNGSGG-ADKGGPTLS-KLGSNSTAQLYPKD-----DGEGRAAAVAMPPASVMTRLI
SEQ ID NO:30    NHRDT--QEDYLEKDEFSFGNR---EMDREMNQLEGEKVGDGK---PKTMPPASVMTRLI
SEQ ID NO:34    GEREPEMDEG--------AKIPASGSPYTCQKKVDMEDGNAN-KNQQMPPASVMTRLI
SEQ ID NO:38    GAVEVEIEDGMMKSPATGLGAKFPVSGSPYVAPRKKGADVPGLEEAAHPMPPASVMTRLI
SEQ ID NO:43    VEMQDQGNNG---------GK-----SPYMGKKGSDVEDGGPGPRKQQMPPASVMTRLI
SEQ ID NO:44    NQ---------YVEREEFSFGNK---DDDSKVLATDGGNNISNKTTQAKVMPPTSVMTRLI
                                                                                                                                      540
```

FIG. 1C

```
SEQ ID NO:14    ********************    *  *   *  *   * *    **   *************
SEQ ID NO:30    LIMVWRKLIRNPNTYSSLIGVVWSLVSYRWGIEMPAIIARSISILSDAGLGMAMFSLGLF
SEQ ID NO:34    LIMVWRKLIRNPNTYSSLIGLTWSLVSLVSFKWNVEMPAIIAKSISILSDAGLGMAMFSLGLF
SEQ ID NO:38    LIMVWRKLIRNPNTYSSLLGLTWSLISFRWHIEMPTIVKGSISILSDAGLGMAMFSLGLF
SEQ ID NO:43    LIMVWRKLIRNPNTYSSLIGLVWSLVSFRWNIQMPTIIKGSISILSDAGLGMAMFSLGLF
SEQ ID NO:44    LIMVWRKLIRNPNTYSSLFGLAWSLVSFKWNIKMPTIMSGSISILSDAGLGMAMFSLGLF
                LIMVWRKLIRNPNSYSSLFGITWSLISFKWNIEMPALIAKSISILSDAGLGMAMFSLGLF
                541                                                         600

SEQ ID NO:14    ***    *  **        *     **       *      **        ***********
SEQ ID NO:30    MALQPRIIACGNKLAAIAMGVREVAGPAVMAAASIAVGLRGVLLHIAIVQAALPQGIVPF
SEQ ID NO:34    MALQPRVIACGNSTAAFAMAVRFLTGPAVMAAASIAVGLKGVLLHVAIVQAAIVQAALPQGIVPF
SEQ ID NO:38    MALQPKIIACGKSVAAFSMAVRFLTGPAVMAAASIAVGLRGVLLHVAIVQAALPQGIVPF
SEQ ID NO:43    MALQPKIIACGKSVATFAMAVRFLTGPAVIAATSIGIGLRGVLLHVAIVQAALPQGIVPF
SEQ ID NO:44    MALQPKIISCGKSVAGEAMAVRFLTGPAVIAATSIAVGLRGVLLHIAIVQAALPQGIVPF
                MALQPKIIACGKSVAGFAMAVRFLTGPAVIAATSIAIGIRGDLLHIAIVQAALPQGIVPF
                MALNPRIIACGNRRAAFAAAAMRFVVGPAVMLVASYAVGLRGVLLHVAIIQAALPQGIVPF
                601                                                         660

SEQ ID NO:14    *******  *  ******** ***      ***  *** ***   *
SEQ ID NO:30    VFAKEYGVHPDILSTA--YG-----PITSHGFITCHS
SEQ ID NO:34    VFAKEYNVHPDILSTAVIFGMLIALPITLVYILLGL
SEQ ID NO:38    VFAKEYNLHADILSTAVIFGMLIALPITILYYLLGV
SEQ ID NO:43    VFAKEYNCHPQILSTAVIFGMLVALPITILYVLLGI
SEQ ID NO:44    VFAKEYNVHPDILSTAVIFGMLVALPVTVLYVLLGL
                VFAKEYNVHPDILSTAVIFGMLIALPITLLYILLGL
                661                                                         697
```

FIG. 1D

SEQUENCE LISTING

<160> NUMBER OF SEQ ID NOS: 48

<210> SEQ ID NO 1
<211> LENGTH: 629
<212> TYPE: DNA
<213> ORGANISM: Zea mays
<220> FEATURE:
<221> NAME/KEY: unsure
<222> LOCATION: (413)
<223> OTHER INFORMATION: n=a,c,g or t
<220> FEATURE:
<221> NAME/KEY: unsure
<222> LOCATION: (466)
<223> OTHER INFORMATION: n=a,c,g or t
<220> FEATURE:
<221> NAME/KEY: unsure
<222> LOCATION: (526)
<223> OTHER INFORMATION: n=a,c,g or t
<220> FEATURE:
<221> NAME/KEY: unsure
<222> LOCATION: (535)
<223> OTHER INFORMATION: n=a,c,g or t
<220> FEATURE:
<221> NAME/KEY: unsure
<222> LOCATION: (549)
<223> OTHER INFORMATION: n=a,c,g or t
<220> FEATURE:
<221> NAME/KEY: unsure
<222> LOCATION: (560)
<223> OTHER INFORMATION: n=a,c,g or t
<220> FEATURE:
<221> NAME/KEY: unsure
<222> LOCATION: (601)..(602)..(603)
<223> OTHER INFORMATION: n=a,c,g or t
<220> FEATURE:
<221> NAME/KEY: unsure
<222> LOCATION: (628)
<223> OTHER INFORMATION: n=a,c,g or t

<400> SEQUENCE: 1

```
gctaaaattg ctaatatttc tccaaaggaa acaagatata taatgtttat cttcagacag    60
catgaagcaa gataagatat atatatatcg attcttcgac cgcagtcagc atgtttgaca   120
gatcgcaatg cctcactcac tgaatcactg aatagatcgc tgtcgtcgga gctatctttc   180
gtttccctac ctaagctaat agtaatcgct aatgctcatc agaaatttca tgtggggccg   240
atacaccaca gcatggcgcc ttccgcacgc tgaagaagcg agcgagagag gctcacagcc   300
ccagcaagat gtagtagacc agggtgatgg gcagagcgat gagcatcccg aagatcacgg   360
ctgtgctcag gatgtcggga tgaacgccgt actccttggg cgaacacgaa cgngcacgat   420 ccctgaggc agagcagcct ggacgatggc gatgtggagg aggagncgcg cagaccgacg   480
gcgatggaag cggcggccat gaccgcgggg gctgcgaaga aaccgnacgc ccatngcgat   540
ggccgccanc ttgttcccgn aagcgatgat cctcgggtgc agcgccatga acaggcctag   600
nnngaacatg gccatccgag accgcgtnc                                     629
```

<210> SEQ ID NO 2
<211> LENGTH: 171
<212> TYPE: PRT
<213> ORGANISM: Zea mays

<400> SEQUENCE: 2

```
Pro Leu Ala Ile Pro Pro Ala Gly Val Met Thr Arg Leu Ile Leu Ile
 1               5                  10                  15

Met Val Trp Arg Lys Leu Ile Arg Asn Pro Asn Thr Tyr Ser Ser Leu
            20                  25                  30
```

Ile Gly Val Val Trp Ser Leu Val Ser Tyr Arg Trp Gly Ile Glu Met
          35                  40                  45

Pro Ala Ile Ile Ala Arg Ser Ile Ser Ile Leu Ser Asp Ala Gly Leu
        50                  55                  60

Gly Met Ala Met Phe Ser Leu Gly Leu Phe Met Ala Leu Gln Pro Arg
65                  70                  75                  80

Ile Ile Ala Cys Gly Asn Lys Leu Ala Ala Ile Ala Met Gly Val Arg
                85                  90                  95

Phe Val Ala Gly Pro Ala Val Met Ala Ala Ser Ile Ala Val Gly
                100                 105                 110

Leu Arg Gly Val Leu Leu His Ile Ala Ile Val Gln Ala Ala Leu Pro
            115                 120                 125

Gln Gly Ile Val Pro Phe Val Phe Ala Lys Glu Tyr Gly Val His Pro
        130                 135                 140

Asp Ile Leu Ser Thr Ala Val Ile Phe Gly Met Leu Ile Ala Leu Pro
145                 150                 155                 160

Ile Thr Leu Val Tyr Tyr Ile Leu Leu Gly Leu
                165                 170

```
<210> SEQ ID NO 3
<211> LENGTH: 1088
<212> TYPE: DNA
<213> ORGANISM: Zea mays
<220> FEATURE:
<221> NAME/KEY: unsure
<222> LOCATION: (110)
<223> OTHER INFORMATION: n=a,c,g or t

<400> SEQUENCE: 3
```

| | | | | | |
|---|---|---|---|---|---|
| gggacgggaa | agccgcggcg | gcgggcgggg | accccagcac | ggtggccgcg | ccgacggcga | 60 |
| tgccgccgac | gagcgtcatg | acccggctga | tcctgatcat | ggtgtggcgn | caactcatcc | 120 |
| gcaacccaaa | cacctactcc | agcctcatcg | gcgtcatctg | gtcgctcgtc | tgcttcaggt | 180 |
| ggaacttcca | gatgccggcc | atcgtcctgc | agtccatctc | catcctgtcg | gacgcggggc | 240 |
| tcgggatggc | catgttcagt | ctcgggctgt | tcatggcgct | gcagccgcgg | atcatcgcgt | 300 |
| gcgggaacaa | ggtggcgacg | ttcgccatgg | cggtgcgctt | cctgaccggt | ccggcggtta | 360 |
| tggcggccgc | gtccttcgcc | gtgggcctcc | gcggcacgct | tctgcacgtc | gccatcgtcc | 420 |
| aggcagctct | gcctcagggc | attgtcccct | tcgtcttcgc | aaaggagtac | aacgtgcacc | 480 |
| ctgacattct | cagcaccgca | gtcatttttg | gcatgctcat | cgccctgccg | atcacgctcg | 540 |
| tctactacat | cctgctcggc | ctgtgaccga | cccgtgggtg | atggcaatgg | catgccccgc | 600 |
| attgctgtaa | ctgtaaagac | cgctgctgcc | actttccgtt | caagggaggc | aagtgaggag | 660 |
| actgtctgct | acgacatttg | cttggcgctt | caaaaatgag | tggcttgttt | ctctctctct | 720 |
| tctatctatt | ttttattttt | tctctagaag | taggtgtgag | gattgtatgg | atggaaagtg | 780 |
| tgggaggtgg | acaagtcgcg | gtagctaggt | aggacgacaa | tggtgaggca | aaacggacca | 840 |
| aaaggaggtg | caagtacaaa | agcttgaagg | gaacaggaga | tccagtttaa | gcacgtcacg | 900 |
| ggatgggttg | atatttcaa | cgggttcagg | gtattttggt | tggctgcgct | gaccgatgta | 960 |
| aaatcagcgc | gccattgtga | caggagatcg | atcttgcttg | agataaacag | ctcacctccg | 1020 |
| gagtttgatg | gcttgagata | agggctcaac | tcaaaataga | cagaaatata | taccgtattt | 1080 |
| gtcactga | | | | | 1088 |

```
<210> SEQ ID NO 4
<211> LENGTH: 187
```

```
<212> TYPE: PRT
<213> ORGANISM: Zea mays

<400> SEQUENCE: 4

Asp Gly Lys Ala Ala Ala Ala Gly Gly Asp Pro Ser Thr Val Ala Ala
  1               5                  10                  15

Pro Thr Ala Met Pro Pro Thr Ser Val Met Thr Arg Leu Ile Leu Ile
             20                  25                  30

Met Val Trp Arg Gln Leu Ile Arg Asn Pro Asn Thr Tyr Ser Ser Leu
         35                  40                  45

Ile Gly Val Ile Trp Ser Leu Val Cys Phe Arg Trp Asn Phe Gln Met
     50                  55                  60

Pro Ala Ile Val Leu Gln Ser Ile Ser Ile Leu Ser Asp Ala Gly Leu
 65                  70                  75                  80

Gly Met Ala Met Phe Ser Leu Gly Leu Phe Met Ala Leu Gln Pro Arg
                 85                  90                  95

Ile Ile Ala Cys Gly Asn Lys Val Ala Thr Phe Ala Met Ala Val Arg
             100                 105                 110

Phe Leu Thr Gly Pro Ala Val Met Ala Ala Ser Phe Ala Val Gly
         115                 120                 125

Leu Arg Gly Thr Leu Leu His Val Ala Ile Val Gln Ala Ala Leu Pro
     130                 135                 140

Gln Gly Ile Val Pro Phe Val Phe Ala Lys Glu Tyr Asn Val His Pro
145                 150                 155                 160

Asp Ile Leu Ser Thr Ala Val Ile Phe Gly Met Leu Ile Ala Leu Pro
                165                 170                 175

Ile Thr Leu Val Tyr Tyr Ile Leu Leu Gly Leu
                180                 185

<210> SEQ ID NO 5
<211> LENGTH: 253
<212> TYPE: DNA
<213> ORGANISM: Zea mays
<220> FEATURE:
<221> NAME/KEY: unsure
<222> LOCATION: (150)
<223> OTHER INFORMATION: n=a,c,g or t
<220> FEATURE:
<221> NAME/KEY: unsure
<222> LOCATION: (164)
<223> OTHER INFORMATION: n=a,c,g or t
<220> FEATURE:
<221> NAME/KEY: unsure
<222> LOCATION: (194)
<223> OTHER INFORMATION: n=a,c,g or t
<220> FEATURE:
<221> NAME/KEY: unsure
<222> LOCATION: (229)
<223> OTHER INFORMATION: n=a,c,g or t
<220> FEATURE:
<221> NAME/KEY: unsure
<222> LOCATION: (237)
<223> OTHER INFORMATION: n=a,c,g or t
<220> FEATURE:
<221> NAME/KEY: unsure
<222> LOCATION: (240)
<223> OTHER INFORMATION: n=a,c,g or t

<400> SEQUENCE: 5
gccccacccc actcatcaca ctctcccacc gcacctcgcc gccgcggggc accgcgccat      60
aaagtgcgtt cccggcctgc acggacgtcg aggagcagct cgcaagtgtt tcttggtgcg    120
tcgatcggca agatgatcac cggcacggan cttctaccac gtcntgacgg ccatggtgcc    180
gttgtacgtt gccntgatcc tggcgtacgg atccgtcagg tggtggcgna tcttcangcn    240
```
gggaccagtg ctc							253

<210> SEQ ID NO 6
<211> LENGTH: 31
<212> TYPE: PRT
<213> ORGANISM: Zea mays
<220> FEATURE:
<221> NAME/KEY: UNSURE
<222> LOCATION: (3)
<223> OTHER INFORMATION: Xaa = ANY AMINO ACID
<220> FEATURE:
<221> NAME/KEY: UNSURE
<222> LOCATION: (8)
<223> OTHER INFORMATION: Xaa = ANY AMINO ACID
<220> FEATURE:
<221> NAME/KEY: UNSURE
<222> LOCATION: (18)
<223> OTHER INFORMATION: Xaa = ANY AMINO ACID

<400> SEQUENCE: 6

Ala Arg Xaa Phe Tyr His Val Xaa Thr Ala Met Val Pro Leu Tyr Val
 1               5                  10                  15

Ala Xaa Ile Leu Ala Tyr Gly Ser Val Arg Trp Trp Arg Ile Phe
            20                  25                  30

<210> SEQ ID NO 7
<211> LENGTH: 624
<212> TYPE: DNA
<213> ORGANISM: Zea mays
<220> FEATURE:
<221> NAME/KEY: unsure
<222> LOCATION: (48)..(49)
<223> OTHER INFORMATION: n=a,c,g or t
<220> FEATURE:
<221> NAME/KEY: unsure
<222> LOCATION: (51)..(52)
<223> OTHER INFORMATION: n=a,c,g or t
<220> FEATURE:
<221> NAME/KEY: unsure
<222> LOCATION: (99)
<223> OTHER INFORMATION: n=a,c,g or t
<220> FEATURE:
<221> NAME/KEY: unsure
<222> LOCATION: (102)..(103)
<223> OTHER INFORMATION: n=a,c,g or t
<220> FEATURE:
<221> NAME/KEY: unsure
<222> LOCATION: (107)..(108)
<223> OTHER INFORMATION: n=a,c,g or t
<220> FEATURE:
<221> NAME/KEY: unsure
<222> LOCATION: (112)
<223> OTHER INFORMATION: n=a,c,g or t
<220> FEATURE:
<221> NAME/KEY: unsure
<222> LOCATION: (114)
<223> OTHER INFORMATION: n=a,c,g or t
<220> FEATURE:
<221> NAME/KEY: unsure
<222> LOCATION: (116)
<223> OTHER INFORMATION: n=a,c,g or t
<220> FEATURE:
<221> NAME/KEY: unsure
<222> LOCATION: (118)
<223> OTHER INFORMATION: n=a,c,g or t
<220> FEATURE:
<221> NAME/KEY: unsure
<222> LOCATION: (129)
<223> OTHER INFORMATION: n=a,c,g or t
<220> FEATURE:
<221> NAME/KEY: unsure
<222> LOCATION: (137)
<223> OTHER INFORMATION: n=a,c,g or t
<220> FEATURE:
<221> NAME/KEY: unsure

```
<222> LOCATION: (389)
<223> OTHER INFORMATION: n=a,c,g or t
<220> FEATURE:
<221> NAME/KEY: unsure
<222> LOCATION: (444)
<223> OTHER INFORMATION: n=a,c,g or t
<220> FEATURE:
<221> NAME/KEY: unsure
<222> LOCATION: (456)
<223> OTHER INFORMATION: n=a,c,g or t
<220> FEATURE:
<221> NAME/KEY: unsure
<222> LOCATION: (490)
<223> OTHER INFORMATION: n=a,c,g or t
<220> FEATURE:
<221> NAME/KEY: unsure
<222> LOCATION: (555)
<223> OTHER INFORMATION: n=a,c,g or t
<220> FEATURE:
<221> NAME/KEY: unsure
<222> LOCATION: (622)
<223> OTHER INFORMATION: n=a,c,g or t

<400> SEQUENCE: 7
ggatggtcca aggagagctt ggggctcgct gccacctcgc gcgccagnnc nnaaataaat    60
cactcccacg cacacccacc accgcgccga gcacctccnc cnnccnncc tncncncncc   120
caccctccnc actagcncta tctagctgag tgaactgaac agcccactgg ctcgtcttag   180
ctaagctcag ctgtaaagct aaggttcgga gtagctagcg tggtggccgg agagtgtagc   240
gagcggcgtt cagctcaccg ggggctgctg ggtgagtgag gaaccagcg tcgtgagagc    300
gctccaagat gattacgggg acggacttct accacgtcat gacggccgtg gtgccgctgt   360
acgtggcgat gatcctggcc tacgggtcng tcggtggtg gcgcatcttc tcgccggaac   420
aatgctccgg gatcaaccgc ttcntggcgc tcttcncggt gccgctgctg tccttccact   480
tcatctccan caacaaccct acaccatgaa cctgcgcttc atcgccgccg aaacctggca   540
aaactcatgg tgctnggcat gctcaccgcg tggaaccact caacgccggg ggaacctgga   600
aattgaacat caagctcttc tnct                                         624

<210> SEQ ID NO 8
<211> LENGTH: 78
<212> TYPE: PRT
<213> ORGANISM: Zea mays
<220> FEATURE:
<221> NAME/KEY: UNSURE
<222> LOCATION: (46)
<223> OTHER INFORMATION: Xaa = ANY AMINO ACID
<220> FEATURE:
<221> NAME/KEY: UNSURE
<222> LOCATION: (50)
<223> OTHER INFORMATION: Xaa = ANY AMINO ACID
<220> FEATURE:
<221> NAME/KEY: UNSURE
<222> LOCATION: (61)
<223> OTHER INFORMATION: Xaa = ANY AMINO ACID

<400> SEQUENCE: 8

Met Ile Thr Gly Thr Asp Phe Tyr His Val Met Thr Ala Val Val Pro
 1               5                  10                  15

Leu Tyr Val Ala Met Ile Leu Ala Tyr Gly Ser Val Arg Trp Trp Arg
                20                  25                  30

Ile Phe Ser Pro Glu Gln Cys Ser Gly Ile Asn Arg Phe Xaa Ala Leu
            35                  40                  45

Phe Xaa Val Pro Leu Leu Ser Phe His Phe Ile Ser Xaa Gln Gln Pro
        50                  55                  60

Tyr Thr Met Asn Leu Arg Phe Ile Ala Ala Glu Thr Trp Gln
```

<210> SEQ ID NO 9
<211> LENGTH: 1426
<212> TYPE: DNA
<213> ORGANISM: Zea mays

<400> SEQUENCE: 9

```
ccacgcgtcc gggatggtcc aaggagagct tggggctcgc tgccacctcg cgcgccagcg      60
cctaaataaa tcactcccac gcacacccac caccgcgccg agcacctcct ccttcccttc     120
cttctctctc ccaccctcct cactagctct atctagctga gtgaactgaa cagcccactg     180
gctcgtctta gctaagctca gctgtaaagc taaggttcgg agtagctagc gtggtggccg     240
gagagtgtag cgagcggcgt tcagctcacc gggggctgct gggtgagtga gggaaccagc     300
gtcgtgagag cgctccaaga tgattacggg gacggacttc taccacgtca tgacggccgt     360
ggtgccgctg tacgtggcga tgatcctggc ctacgggtcg gtgcggtggt ggcgcatctt     420
ctcgccggac cagtgctccg ggatcaaccg cttcgtggcg ctcttcgcgg tgccgctgct     480
gtccttccac ttcatctcca ccaacaaccc ctacaccatg aacctgcgct tcatcgccgc     540
cgacacgctg cagaagctca tggtgctggc catgctcacc gcgtggagcc acctcagccg     600
ccggggcagc ctggagtgga ccatcacgct cttctccctc tccacgctgc caacacgct     660
cgtcatgggc atccccctgc tcaagggcat gtacggcgac ttctccggca gcctcatggt     720
gcagatcgtc gtgctccagt gcatcatctg gtacacgctc atgctcttca tgttcgagta     780
ccgcggcgcg cggatgctca tcaccgagca gttcccggac aacgccgggg ccatcgcctc     840
catcgtcgtc gacccggacg tggtctccct cgacggccgc agggacgcca tcgagacgga     900
ggccgaggtc aaggaggacg gcaggataca cgtcaccgtg cgccgctcca acgcctcgcg     960
ctccgacatc tactcgcgcc gctccatggg cttctccagc accacgccgc gcccagcaa    1020
cctgaccaac gccgagatct actcgctgca gtcgtcgcgc aacccgaccc cgcggggctc    1080
cagcttcaac cacaacgact tctactccat ggtcggccgc agctccaact tcggcgcggc    1140
cgacgcgttc ggcatccgca ccggcgccac gccgcgcccg tccaactacg aggacgacgc    1200
gtccaagccc aagtaccctc tccccgtggt gaatgcgacg tccggggcgg gggcggctca    1260
ctaccccgcg ccgaacccgg ccgtggccgc ggcgcccaag ggcgcaggaa aggcggcgac    1320
gaacgggcag gccaagggcg aggacctcca catgttcgtc tggagctcca gcgcgtcgcc    1380
cgtgtcggac gtcttcggcg gtggcgcccc ggactacaac gaggcc                  1426
```

<210> SEQ ID NO 10
<211> LENGTH: 369
<212> TYPE: PRT
<213> ORGANISM: Zea mays

<400> SEQUENCE: 10

```
Met Ile Thr Gly Thr Asp Phe Tyr His Val Met Thr Ala Val Val Pro
  1               5                  10                  15

Leu Tyr Val Ala Met Ile Leu Ala Tyr Gly Ser Val Arg Trp Trp Arg
             20                  25                  30

Ile Phe Ser Pro Asp Gln Cys Ser Gly Ile Asn Arg Phe Val Ala Leu
         35                  40                  45

Phe Ala Val Pro Leu Leu Ser Phe His Phe Ile Ser Thr Asn Asn Pro
     50                  55                  60

Tyr Thr Met Asn Leu Arg Phe Ile Ala Ala Asp Thr Leu Gln Lys Leu
 65                  70                  75                  80
```

```
Met Val Leu Ala Met Leu Thr Ala Trp Ser His Leu Ser Arg Arg Gly
                85                  90                  95

Ser Leu Glu Trp Thr Ile Thr Leu Phe Ser Leu Ser Thr Leu Pro Asn
            100                 105                 110

Thr Leu Val Met Gly Ile Pro Leu Leu Lys Gly Met Tyr Gly Asp Phe
        115                 120                 125

Ser Gly Ser Leu Met Val Gln Ile Val Leu Gln Cys Ile Ile Trp
    130                 135                 140

Tyr Thr Leu Met Leu Phe Met Phe Glu Tyr Arg Gly Ala Arg Met Leu
145                 150                 155                 160

Ile Thr Glu Gln Phe Pro Asp Asn Ala Gly Ala Ile Ala Ser Ile Val
                165                 170                 175

Val Asp Pro Asp Val Val Ser Leu Asp Gly Arg Arg Asp Ala Ile Glu
            180                 185                 190

Thr Glu Ala Glu Val Lys Glu Asp Gly Arg Ile His Val Thr Val Arg
        195                 200                 205

Arg Ser Asn Ala Ser Arg Ser Asp Ile Tyr Ser Arg Arg Ser Met Gly
    210                 215                 220

Phe Ser Ser Thr Thr Pro Arg Pro Ser Asn Leu Thr Asn Ala Glu Ile
225                 230                 235                 240

Tyr Ser Leu Gln Ser Ser Arg Asn Pro Thr Pro Arg Gly Ser Ser Phe
                245                 250                 255

Asn His Asn Asp Phe Tyr Ser Met Val Gly Arg Ser Ser Asn Phe Gly
            260                 265                 270

Ala Ala Asp Ala Phe Gly Ile Arg Thr Gly Ala Thr Pro Arg Pro Ser
        275                 280                 285

Asn Tyr Glu Asp Asp Ala Ser Lys Pro Lys Tyr Pro Leu Pro Val Val
    290                 295                 300

Asn Ala Thr Ser Gly Ala Gly Ala Ala His Tyr Pro Ala Pro Asn Pro
305                 310                 315                 320

Ala Val Ala Ala Ala Pro Lys Gly Ala Arg Lys Ala Ala Thr Asn Gly
                325                 330                 335

Gln Ala Lys Gly Glu Asp Leu His Met Phe Val Trp Ser Ser Ser Ala
            340                 345                 350

Ser Pro Val Ser Asp Val Phe Gly Gly Gly Ala Pro Asp Tyr Asn Glu
        355                 360                 365

Ala

<210> SEQ ID NO 11
<211> LENGTH: 504
<212> TYPE: DNA
<213> ORGANISM: Zea mays
<220> FEATURE:
<221> NAME/KEY: unsure
<222> LOCATION: (126)
<223> OTHER INFORMATION: n=a,c,g or t
<220> FEATURE:
<221> NAME/KEY: unsure
<222> LOCATION: (192)
<223> OTHER INFORMATION: n=a,c,g or t
<220> FEATURE:
<221> NAME/KEY: unsure
<222> LOCATION: (205)
<223> OTHER INFORMATION: n=a,c,g or t
<220> FEATURE:
<221> NAME/KEY: unsure
<222> LOCATION: (237)
<223> OTHER INFORMATION: n=a,c,g or t
<220> FEATURE:
<221> NAME/KEY: unsure
```

```
<222> LOCATION: (242)
<223> OTHER INFORMATION: n=a,c,g or t
<220> FEATURE:
<221> NAME/KEY: unsure
<222> LOCATION: (244)
<223> OTHER INFORMATION: n=a,c,g or t
<220> FEATURE:
<221> NAME/KEY: unsure
<222> LOCATION: (255)
<223> OTHER INFORMATION: n=a,c,g or t
<220> FEATURE:
<221> NAME/KEY: unsure
<222> LOCATION: (258)
<223> OTHER INFORMATION: n=a,c,g or t
<220> FEATURE:
<221> NAME/KEY: unsure
<222> LOCATION: (263)
<223> OTHER INFORMATION: n=a,c,g or t
<220> FEATURE:
<221> NAME/KEY: unsure
<222> LOCATION: (265)
<223> OTHER INFORMATION: n=a,c,g or t
<220> FEATURE:
<221> NAME/KEY: unsure
<222> LOCATION: (287)
<223> OTHER INFORMATION: n=a,c,g or t
<220> FEATURE:
<221> NAME/KEY: unsure
<222> LOCATION: (430)
<223> OTHER INFORMATION: n=a,c,g or t
<220> FEATURE:
<221> NAME/KEY: unsure
<222> LOCATION: (449)
<223> OTHER INFORMATION: n=a,c,g or t
<220> FEATURE:
<221> NAME/KEY: unsure
<222> LOCATION: (455)
<223> OTHER INFORMATION: n=a,c,g or t
<220> FEATURE:
<221> NAME/KEY: unsure
<222> LOCATION: (488)
<223> OTHER INFORMATION: n=a,c,g or t
<220> FEATURE:
<221> NAME/KEY: unsure
<222> LOCATION: (490)
<223> OTHER INFORMATION: n=a,c,g or t

<400> SEQUENCE: 11 tttttgagc cctacaacca ctctcttctt cattgctcca cactaccatc tcatctctcc      60
gccattttac accactccct tctcgttgca acccaacaaa ttggcactgc tcgtcgccga     120
cccctnctcc ctccccgcgt cccccgacaa gccatccgcg ccatgatca ccgcgctgga      180 cctctaccac gngctgacgg ctggnggtgc cgctgtacgt ggccatgacg ctggcgnacg     240
gntncgtccg ctggnggngc atntncacgc cggaccagtg ctccggnatc aaccgcttcg     300
tggcgctctt cgccgtgccg ctcctctcct tccacttcat ctccaccaac gaccccttcg     360
ccatgaacct gcgcttcctg gccgtcgaca cgctgcagaa ggtggccgtc ctcgcgctgc     420
tggcgctggn ctcccgcggc ctcttctcnc cgagngcgct cagggctcga ctggagcatc     480
aagctctncn ccctctccac gctc                                            504

<210> SEQ ID NO 12
<211> LENGTH: 114
<212> TYPE: PRT
<213> ORGANISM: Zea mays
<220> FEATURE:
<221> NAME/KEY: UNSURE
<222> LOCATION: (10)
<223> OTHER INFORMATION: Xaa = ANY AMINO ACID
<220> FEATURE:
<221> NAME/KEY: UNSURE
<222> LOCATION: (14)
<223> OTHER INFORMATION: Xaa = ANY AMINO ACID
```

```
<220> FEATURE:
<221> NAME/KEY: UNSURE
<222> LOCATION: (25)
<223> OTHER INFORMATION: Xaa = ANY AMINO ACID
<220> FEATURE:
<221> NAME/KEY: UNSURE
<222> LOCATION: (27)
<223> OTHER INFORMATION: Xaa = ANY AMINO ACID
<220> FEATURE:
<221> NAME/KEY: UNSURE
<222> LOCATION: (31)..(32)..(33)..(34)
<223> OTHER INFORMATION: Xaa = ANY AMINO ACID
<220> FEATURE:
<221> NAME/KEY: UNSURE
<222> LOCATION: (89)
<223> OTHER INFORMATION: Xaa = ANY AMINO ACID
<220> FEATURE:
<221> NAME/KEY: UNSURE
<222> LOCATION: (91)
<223> OTHER INFORMATION: Xaa = ANY AMINO ACID
<220> FEATURE:
<221> NAME/KEY: UNSURE
<222> LOCATION: (96)
<223> OTHER INFORMATION: Xaa = ANY AMINO ACID
<220> FEATURE:
<221> NAME/KEY: UNSURE
<222> LOCATION: (98)
<223> OTHER INFORMATION: Xaa = ANY AMINO ACID
<220> FEATURE:
<221> NAME/KEY: UNSURE
<222> LOCATION: (109)..(110)
<223> OTHER INFORMATION: Xaa = ANY AMINO ACID

<400> SEQUENCE: 12

Met Ile Thr Ala Leu Asp Leu Tyr His Xaa Leu Thr Ala Xaa Val Pro
 1               5                  10                  15

Leu Tyr Val Ala Met Thr Leu Ala Xaa Gly Xaa Val Arg Trp Xaa Xaa
                20                  25                  30

Xaa Xaa Thr Pro Asp Gln Cys Ser Gly Ile Asn Arg Phe Val Ala Leu
            35                  40                  45

Phe Ala Val Pro Leu Leu Ser Phe His Phe Ile Ser Thr Asn Asp Pro
 50                  55                  60

Phe Ala Met Asn Leu Arg Phe Leu Ala Val Asp Thr Leu Gln Lys Val
 65                  70                  75                  80

Ala Val Leu Ala Leu Leu Ala Leu Xaa Ser Xaa Ala Ala Ser Ser Xaa
                85                  90                  95

Arg Xaa Arg Ser Gly Leu Asp Trp Ser Ile Lys Leu Xaa Xaa Leu Ser
            100                 105                 110

Thr Leu

<210> SEQ ID NO 13
<211> LENGTH: 2769
<212> TYPE: DNA
<213> ORGANISM: Zea mays

<400> SEQUENCE: 13
ccacgcgtcc gctgagccct acaaccactc tcttcttcat tgctccacac taccatctca     60
tctctccgcc attttacacc actcccttct cgttgcaacc caacaaattg cactgctcg    120 tcgccgaccc ctcctccctc cccgcgtccc ccgacaagcc atccgcggcc atgatcaccg    180
cgctggacct ctaccacgtg ctgacggcgg tggtgccgct gtacgtggcc atgacgctgg    240
cgtacggctc cgtccgctgg tggcgcatct tcacgccgga ccagtgctcc gggatcaacc    300
gcttcgtggc gctcttcgcc gtgccgctcc tcctccttca cttcatctcc accaacgacc    360
ccttcgccat gaacctgcgc ttcctggccg ccgacacgct gcagaaggtg gccgtcctcg    420
```

-continued

```
cgctgctggc gctggcctcc cgcggcctct cctccccgcg cgcgctcggg ctcgactgga      480
gcatcacgct cttctccctc tccacgctcc caacacgct cgtcatgggc atcccgctgc       540
tgcgaggcat gtacggcgcg tcgtcggccg gcacgctcat ggtccaggtc gtcgtcctcc      600
agtgcatcat ctggtacacg ctcatgctct tcctcttcga gtaccgcgcc gcgcgcgcgc      660
tcgtcctcga ccagttcccc gacggcgccg ccgcgtccat cgtctccttc cgcgtcgact      720
ccgacgtcgt ctcgctcgcc agggggggacg tcgagctcga ggccgagccc gacggcgtcg     780
ccggcgccgg cgccgtctcc tcccgcggcg gggacgccgg gcgggtgcgc gtcaccgtgc      840
gcaagtccac cagctcgcgc tccgaggccg cgtgctcgca ctcgcactcc cagaccatgc      900
agccccgtgt gtccaacctc tccggcgtgg agatctactc gctgcagtcg tcgcgcaacc      960
ccaccccgcg cgggtccagc ttcaaccacg ccgacttctt caacatcgtc ggcgccgccg     1020
ccaagggagg cggaggagcg gcgggggacg aggagaaggg cgcatgcggc ggcggcggcg     1080
gaggacactc gccgcagccg caggccgtcg ccgtgccggc caagaggaag gacctgcaca     1140
tgctcgtctg gagctccagc gcctcgcccg tgtccgagcg cgccgccgtg cacgtcttcg     1200
gcgccggcgg cgctgaccat gccgacgtcc tcgccaaagg agcccaggcc tacgacgagt     1260
acgggcgcga cgactacagc agcaggacga agaacgggag cggcggcgcg gacaagggcg     1320
ggccgacgct gtcgaagctg gggtccaact cgacggcgca gctgtacccc aaggacgacg     1380
gcgaggggag ggcggcggcg gtggcgatgc cgccggcgag cgtgatgacg cggctcatcc     1440
tcatcatggt gtggaggaag ctgatccgga accccaacac ctactccagc ctcatcggcg     1500
tcgtctggtc cctggtctcc tacaggtggg gcatcgagat gccagcgatc atcgcccggt     1560
cgatttcgat cctgtcggac gcgggtctcg ggatggccat gttcagccta ggcctgttca     1620
tggcgctgca gccgaggatc atcgcgtgcg ggaacaagct ggcggccatc gcgatgggcg     1680
tccggttcgt cgcaggcccc gcggtcatgg ccgccgcctc catcgccgtc ggtctgcgcg     1740
gcgtcctcct ccacatcgcc atcgtccagg ctgctctgcc tcaggggatc gtgccgttcg     1800
tgttcgccaa ggagtacggc gttcatcccg acatcctgag cacagcgtat ggtccaataa     1860
catcgcatgg tttcatcact tgccatagtt aacgggaaaa aaaagcagaa gcaatcgatg     1920
acgacgcact gaattcacta tgattcatta ctaatgatgg tgtgttcatg cagtgcagtc     1980
aaagaaccac taataagcac tgatctagga cagcatcagc atgattgatt gcttgttttc     2040
tcctgacaat ctgcatttct tactacacag tgtgccttca ctcatccatc cagatgatca     2100
tacaacacta ctgatgcatc ttttttttg attctgctgc agcgtgatct tcgggatgct     2160
catcgctctg cccatcaccc tggtctacta catcttgctg gggctgtgag cctctctcgc     2220
tcgcttcttc agcgtgcgga aggcgccatg ctgtggtgta tcggcccac atgaaatttc     2280 tgatgagcat tagcgattac tattagctta gcgaagaatg atgagatggt gtcggcctgt     2340
cgggactggg ggagtcagac cagaccccccc tcgaacaaaa gtttcttttg gcttctgtcc     2400
gtcagaaaca aaagttttgg cttttggcat gcgcactcga agcacagcag cagcagcagc     2460
atcatccatg agatgatact cctctcgaat cctagagcta gcgaaggcaa taataagata     2520
ccacaaggca atggaatcaa caaaagcttc atgcgacgcg ctatcatatc aaggaacaca     2580
tgcagaatac aacggagtct agtgcgcaat ggcttcttct ctttttttt cttgcgaaaa      2640 gggtttctag actgattaaa ggattccaaa tagcatctct ggattcgatt tctttcgcag     2700
acaaattttc tggcttttt agaaaaatcc tctcgttgaa aaaaaaaaa aaaaaaaaa        2760 aaaaaaaag                                                            2769
```

```
<210> SEQ ID NO 14
<211> LENGTH: 573
<212> TYPE: PRT
<213> ORGANISM: Zea mays

<400> SEQUENCE: 14

Met Ile Thr Ala Leu Asp Leu Tyr His Val Leu Thr Ala Val Val Pro
 1               5                  10                  15

Leu Tyr Val Ala Met Thr Leu Ala Tyr Gly Ser Val Arg Trp Trp Arg
            20                  25                  30

Ile Phe Thr Pro Asp Gln Cys Ser Gly Ile Asn Arg Phe Val Ala Leu
        35                  40                  45

Phe Ala Val Pro Leu Leu Ser Phe His Phe Ile Ser Thr Asn Asp Pro
    50                  55                  60

Phe Ala Met Asn Leu Arg Phe Leu Ala Ala Asp Thr Leu Gln Lys Val
65                  70                  75                  80

Ala Val Leu Ala Leu Leu Ala Leu Ala Ser Arg Gly Leu Ser Ser Pro
                85                  90                  95

Arg Ala Leu Gly Leu Asp Trp Ser Ile Thr Leu Phe Ser Leu Ser Thr
            100                 105                 110

Leu Pro Asn Thr Leu Val Met Gly Ile Pro Leu Leu Arg Gly Met Tyr
        115                 120                 125

Gly Ala Ser Ser Ala Gly Thr Leu Met Val Gln Val Val Leu Gln
    130                 135                 140

Cys Ile Ile Trp Tyr Thr Leu Met Leu Phe Leu Phe Glu Tyr Arg Ala
145                 150                 155                 160

Ala Arg Ala Leu Val Leu Asp Gln Phe Pro Asp Gly Ala Ala Ala Ser
                165                 170                 175

Ile Val Ser Phe Arg Val Asp Ser Asp Val Val Ser Leu Ala Arg Gly
            180                 185                 190

Asp Val Glu Leu Glu Ala Glu Pro Asp Gly Val Ala Gly Ala Gly Ala
        195                 200                 205

Val Ser Ser Arg Gly Gly Asp Ala Gly Arg Val Arg Val Thr Val Arg
    210                 215                 220

Lys Ser Thr Ser Ser Arg Ser Glu Ala Ala Cys Ser His Ser His Ser
225                 230                 235                 240

Gln Thr Met Gln Pro Arg Val Ser Asn Leu Ser Gly Val Glu Ile Tyr
                245                 250                 255

Ser Leu Gln Ser Ser Arg Asn Pro Thr Pro Arg Gly Ser Ser Phe Asn
            260                 265                 270

His Ala Asp Phe Phe Asn Ile Val Gly Ala Ala Ala Lys Gly Gly Gly
        275                 280                 285

Gly Ala Ala Gly Asp Glu Glu Lys Gly Ala Cys Gly Gly Gly Gly
    290                 295                 300

Gly His Ser Pro Gln Pro Gln Ala Val Ala Val Pro Ala Lys Arg Lys
305                 310                 315                 320

Asp Leu His Met Leu Val Trp Ser Ser Ser Ala Ser Pro Val Ser Glu
                325                 330                 335

Arg Ala Ala Val His Val Phe Gly Ala Gly Gly Ala Asp His Ala Asp
            340                 345                 350

Val Leu Ala Lys Gly Ala Gln Ala Tyr Asp Glu Tyr Gly Arg Asp Asp
        355                 360                 365

Tyr Ser Ser Arg Thr Lys Asn Gly Ser Gly Gly Ala Asp Lys Gly Gly
    370                 375                 380
```

```
Pro Thr Leu Ser Lys Leu Gly Ser Asn Ser Thr Ala Gln Leu Tyr Pro
385                 390                 395                 400

Lys Asp Asp Gly Glu Gly Arg Ala Ala Val Ala Met Pro Pro Ala
                405                 410                 415

Ser Val Met Thr Arg Leu Ile Leu Ile Met Val Trp Arg Lys Leu Ile
            420                 425                 430

Arg Asn Pro Asn Thr Tyr Ser Ser Leu Ile Gly Val Val Trp Ser Leu
            435                 440                 445

Val Ser Tyr Arg Trp Gly Ile Glu Met Pro Ala Ile Ala Arg Ser
        450                 455                 460

Ile Ser Ile Leu Ser Asp Ala Gly Leu Gly Met Ala Met Phe Ser Leu
465                 470                 475                 480

Gly Leu Phe Met Ala Leu Gln Pro Arg Ile Ile Ala Cys Gly Asn Lys
                485                 490                 495

Leu Ala Ala Ile Ala Met Gly Val Arg Phe Val Ala Gly Pro Ala Val
                500                 505                 510

Met Ala Ala Ala Ser Ile Ala Val Gly Leu Arg Gly Val Leu Leu His
                515                 520                 525

Ile Ala Ile Val Gln Ala Ala Leu Pro Gln Gly Ile Val Pro Phe Val
530                 535                 540

Phe Ala Lys Glu Tyr Gly Val His Pro Asp Ile Leu Ser Thr Ala Tyr
545                 550                 555                 560

Gly Pro Ile Thr Ser His Gly Phe Ile Thr Cys His Ser
                565                 570

<210> SEQ ID NO 15
<211> LENGTH: 543
<212> TYPE: DNA
<213> ORGANISM: Oryza sativa
<220> FEATURE:
<221> NAME/KEY: unsure
<222> LOCATION: (42)
<223> OTHER INFORMATION: n=a,c,g or t
<220> FEATURE:
<221> NAME/KEY: unsure
<222> LOCATION: (374)
<223> OTHER INFORMATION: n=a,c,g or t
<220> FEATURE:
<221> NAME/KEY: unsure
<222> LOCATION: (412)
<223> OTHER INFORMATION: n=a,c,g or t
<220> FEATURE:
<221> NAME/KEY: unsure
<222> LOCATION: (415)
<223> OTHER INFORMATION: n=a,c,g or t
<220> FEATURE:
<221> NAME/KEY: unsure
<222> LOCATION: (431)
<223> OTHER INFORMATION: n=a,c,g or t
<220> FEATURE:
<221> NAME/KEY: unsure
<222> LOCATION: (443)
<223> OTHER INFORMATION: n=a,c,g or t
<220> FEATURE:
<221> NAME/KEY: unsure
<222> LOCATION: (463)
<223> OTHER INFORMATION: n=a,c,g or t
<220> FEATURE:
<221> NAME/KEY: unsure
<222> LOCATION: (475)
<223> OTHER INFORMATION: n=a,c,g or t
<220> FEATURE:
<221> NAME/KEY: unsure
<222> LOCATION: (482)
<223> OTHER INFORMATION: n=a,c,g or t
<220> FEATURE:
<221> NAME/KEY: unsure
<222> LOCATION: (511)
```

```
<223> OTHER INFORMATION: n=a,c,g or t
<220> FEATURE:
<221> NAME/KEY: unsure
<222> LOCATION: (514)
<223> OTHER INFORMATION: n=a,c,g or t
<220> FEATURE:
<221> NAME/KEY: unsure
<222> LOCATION: (519)
<223> OTHER INFORMATION: n=a,c,g or t
<220> FEATURE:
<221> NAME/KEY: unsure
<222> LOCATION: (521)
<223> OTHER INFORMATION: n=a,c,g or t
<220> FEATURE:
<221> NAME/KEY: unsure
<222> LOCATION: (530)
<223> OTHER INFORMATION: n=a,c,g or t
<220> FEATURE:
<221> NAME/KEY: unsure
<222> LOCATION: (535)
<223> OTHER INFORMATION: n=a,c,g or t
<220> FEATURE:
<221> NAME/KEY: unsure
<222> LOCATION: (543)
<223> OTHER INFORMATION: n=a,c,g or t

<400> SEQUENCE: 15
gagcgacgtc gagatgaacg gcgccgtcgt cgcggcgccg gngcggcggc ggcggcgtcc      60
ggctaccgtt ctgggcgacg gcgaggacgg tggggctgaa gctggcgagg aacccgaacg     120
tgtacgccag cgttctcggc gtcgtgtggg cgtgcatcgc gtacaggtgg cacctgagct     180
tgccggggat cgtgacgggg tcgctgcagg tgatgtccag gactggcacg gggatgtcca     240
tgttcagcat ggggttgttc atgggcagc aggagagggt gatagcgtgc ggggcggggc      300
tgacggcgct ggggatggcg ctgccggttcg tcgccggtcc gctcgccacg ctcgtcggcg    360
ccgccgccct cggnctccgc ggcgacgtcc tgcacctcgc catcatacag gncgnactgc     420
tcaatcgatt nttcttcgtt ttncaaagga gtatggctta ttncgatgac tcagnacggc    480
gntatattcg gacattatcc tgtgcgatct nttnaatang nggtttgggn ttgtnaaatc    540 atn                                                                   543

<210> SEQ ID NO 16
<211> LENGTH: 110
<212> TYPE: PRT
<213> ORGANISM: Oryza sativa
<220> FEATURE:
<221> NAME/KEY: UNSURE
<222> LOCATION: (108)..(109)
<223> OTHER INFORMATION: Xaa = ANY AMINO ACID

<400> SEQUENCE: 16

Val Gly Leu Lys Leu Ala Arg Asn Pro Asn Val Tyr Ala Ser Val Leu
 1               5                  10                  15

Gly Val Val Trp Ala Cys Ile Ala Tyr Arg Trp His Leu Ser Leu Pro
            20                  25                  30

Gly Ile Val Thr Gly Ser Leu Gln Val Met Ser Arg Thr Gly Thr Gly
        35                  40                  45

Met Ser Met Phe Ser Met Gly Leu Phe Met Gly Gln Gln Glu Arg Val
    50                  55                  60

Ile Ala Cys Gly Ala Gly Leu Thr Ala Leu Gly Met Ala Leu Arg Phe
65                  70                  75                  80

Val Ala Gly Pro Leu Ala Thr Leu Val Gly Ala Ala Ala Leu Gly Leu
                85                  90                  95

Arg Gly Asp Val Leu His Leu Ala Ile Ile Gln Xaa Xaa Leu
            100                 105                 110
```

<210> SEQ ID NO 17
<211> LENGTH: 330
<212> TYPE: DNA
<213> ORGANISM: Oryza sativa

<400> SEQUENCE: 17

| | | | | | |
|---|---|---|---|---|---|
| ctccactcgg | ccgctcctgc | atgtataact | agctagttct | agctcgctca | ggcactcgat | 60 |
| ccaccgccgg | gcgcgttgga | ttgagatagg | ctgaggagat | gatatccggg | cacgacttct | 120 |
| acacggtgat | ggcggcggtg | gtgccgctgt | acgtggcgat | gttcctggcg | tacgggtcgg | 180 |
| tgcggtggtg | gggcatcttc | acgccggacc | agtgctccgg | catcaaccgc | ttcgtcgcca | 240 |
| tcttcgccgt | gccgctcctg | tccttccact | tcatctccac | caacgacccg | tacgccatga | 300 |
| acctccgctt | cctggcggcg | ggacacgctg | | | | 330 |

<210> SEQ ID NO 18
<211> LENGTH: 74
<212> TYPE: PRT
<213> ORGANISM: Oryza sativa

<400> SEQUENCE: 18

Met Ile Ser Gly His Asp Phe Tyr Thr Val Met Ala Ala Val Val Pro
 1               5                  10                  15
Leu Tyr Val Ala Met Phe Leu Ala Tyr Gly Ser Val Arg Trp Trp Gly
             20                  25                  30
Ile Phe Thr Pro Asp Gln Cys Ser Gly Ile Asn Arg Phe Val Ala Ile
         35                  40                  45
Phe Ala Val Pro Leu Leu Ser Phe His Phe Ile Ser Thr Asn Asp Pro
     50                  55                  60
Tyr Ala Met Asn Leu Arg Phe Leu Ala Ala
 65                  70

<210> SEQ ID NO 19
<211> LENGTH: 2162
<212> TYPE: DNA
<213> ORGANISM: Oryza sativa

<400> SEQUENCE: 19

| | | | | | |
|---|---|---|---|---|---|
| ctccactcgg | ccgctcctgc | atgtataact | agctagttct | agctcgctca | ggcactcgat | 60 |
| ccaccgccgg | gcgcgttgga | ttgagatagg | ctgaggagat | gatatccggg | cacgacttct | 120 |
| acacggtgat | ggcggcggtg | gtgccgctgt | acgtggcgat | gttcctggcg | tacgggtcgg | 180 |
| tgcggtggtg | gggcatcttc | acgccggacc | agtgctccgg | catcaaccgc | ttcgtcgcca | 240 |
| tcttcgccgt | gccgctcctg | tccttccact | tcatctccac | caacgacccg | tacgccatga | 300 |
| acctccgctt | cctggcggcg | ggacacgctg | cagaagctgct | cgtcctggcg | gggctcgccg | 360 |
| cgtggtcgcg | cctcccctcg | cggaccggcg | cgccgcggct | ggactggtcc | atcacgctct | 420 |
| tctccctctc | cacgctgccc | aacacgctcg | tcatggggat | cccgctgctg | atcgccatgt | 480 |
| acgggccata | tccggctcg | ctcatggtcc | agatcgtcgt | gctccagtgc | atcatctggt | 540 |
| acacgctgat | gctcttcctc | ttcgagttcc | gcgccgcgcg | gatgctgatc | gccgaccagt | 600 |
| tcccggacac | ggcggcgtcc | atcgtgtccc | tgcacgtcga | cccggacgtg | gtgtcgctgg | 660 |
| agggcggcca | cgcggagacg | gaggccgagg | tggcggcgga | cgggcggctg | cacgtcaccg | 720 |
| tgcgccggtc | ctcggtgtcg | cggcggtcgc | tgctggtcac | gccgcggccg | tcgaacctga | 780 |
| cgggagcgga | gatctactcg | cttagctcgt | cgcggaaccc | aaccccgcgg | ggctccaact | 840 |

-continued

```
tcaaccacgc cgacttcttc gccatggtcg gcggcgggcc accgccccg acgcccgctg      900
cggtgcgcgg ctcgagcttc ggcgcctccg agctttactc gctgcaatcg tcgcggggcc      960
caaccccgag gcagtccaac ttcgacgagc actcggcacg gccgccgaaa ccaccggcaa     1020
cgaccacggg ggcactcaac cacgatgcca aggagctcca catgttcgtg tggagctcga     1080
gcgcgtctcc cgtctcagaa gtcagcggcc tgcctgtgtt cagtggcggc ggcggcggcg     1140
gcgctctcga cgtcggcgcc aaggaaatcc acatggtcat ccccgccgac ctgccgcaga     1200
acaacggctc aggcaaagag cacgaggagt acggcgcagt ggcattgggt ggcggcggcg     1260
gcggagagaa cttcagcttc ggaggcggca agacggtgga cggcgccgag gcagtagacg     1320
aggaggcggc cttgcctgac gggctgacga agatggggtc gagctcgacg gcggagctgc     1380
acccgaaggt cgtcgacgtc gacggaccga acgccggcgg cggcgccgcg ggcgcggggc     1440
agtaccaaat gccgccggcg agcgtgatga cacgcctcat cctcataatg gtgtggcgca     1500
agctcatccg caaccccaac acttactcca gcctcctcgg cctcgcctgg tccctcgtcg     1560
ccttccggat tgttcatggc gctgcagccc agcatcatcg cgtgtggcaa atcagccgcc     1620
gtcgtctcca tggccgtccg cttcctcgcg ggccctgccg tcatggccgc cgcgtcaatc     1680
gccatcggac tccgcgggac gctcctgcac gtcgccattg ttcaggcggc tctaccacaa     1740
gggattgtgc cttttgtttt tgcaaaagaa tacaatgtcc acccggccat cctgagcaca     1800
gcggtaattt ttggcatgct aatagctctt ccaatcacat tgctgtacta catccttctt     1860
ggactatgat caagaaagct tatggacgct ctcacataaa acggaagaaa tgggggcaaa     1920
gagagagaaa aaaaagcgat cctgtccatc tcaaacagcg tatgcttata tgtatagcct     1980
gttgtcggac attgcccatg atgacaagac aacgaagttg ttacagagct atatatctct     2040
gcgacatttg tacaagagat aacgacagaa tgtactcaaa tataaccgat attagatatg     2100
tgttctgtta aagatctcaa aaaaaaaaaa aaaaaaaaaa aaaaaaaaaa aaaaaaaaaa     2160
aa                                                                  2162
```

<210> SEQ ID NO 20
<211> LENGTH: 589
<212> TYPE: PRT
<213> ORGANISM: Oryza sativa

<400> SEQUENCE: 20

```
Met Ile Ser Gly His Asp Phe Tyr Thr Val Met Ala Ala Val Val Pro
  1               5                  10                  15

Leu Tyr Val Ala Met Phe Leu Ala Tyr Gly Ser Val Arg Trp Trp Gly
             20                  25                  30

Ile Phe Thr Pro Asp Gln Cys Ser Gly Ile Asn Arg Phe Val Ala Ile
         35                  40                  45

Phe Ala Val Pro Leu Leu Ser Phe His Phe Ile Ser Thr Asn Asp Pro
     50                  55                  60

Tyr Ala Met Asn Leu Arg Phe Leu Ala Ala Asp Thr Leu Gln Lys Leu
 65                  70                  75                  80

Leu Val Leu Ala Gly Leu Ala Ala Trp Ser Arg Leu Pro Ser Arg Thr
                 85                  90                  95

Gly Ala Pro Arg Leu Asp Trp Ser Ile Thr Leu Phe Ser Leu Ser Thr
            100                 105                 110

Leu Pro Asn Thr Leu Val Met Gly Ile Pro Leu Leu Ile Ala Met Tyr
        115                 120                 125

Gly Pro Tyr Ser Gly Ser Leu Met Val Gln Ile Val Val Leu Gln Cys
    130                 135                 140
```

```
Ile Ile Trp Tyr Thr Leu Met Leu Phe Leu Phe Glu Phe Arg Ala Ala
145                 150                 155                 160

Arg Met Leu Ile Ala Asp Gln Phe Pro Asp Thr Ala Ala Ser Ile Val
                165                 170                 175

Ser Leu His Val Asp Pro Asp Val Val Ser Leu Glu Gly Gly His Ala
            180                 185                 190

Glu Thr Glu Ala Glu Val Ala Ala Asp Gly Arg Leu His Val Thr Val
                195                 200                 205

Arg Arg Ser Ser Val Ser Arg Arg Ser Leu Leu Val Thr Pro Arg Pro
210                 215                 220

Ser Asn Leu Thr Gly Ala Glu Ile Tyr Ser Leu Ser Ser Arg Asn
225                 230                 235                 240

Pro Thr Pro Arg Gly Ser Asn Phe Asn His Ala Asp Phe Phe Ala Met
                245                 250                 255

Val Gly Gly Gly Pro Pro Pro Thr Pro Ala Ala Val Arg Gly Ser
                260                 265                 270

Ser Phe Gly Ala Ser Glu Leu Tyr Ser Leu Gln Ser Ser Arg Gly Pro
        275                 280                 285

Thr Pro Arg Gln Ser Asn Phe Asp Glu His Ser Ala Arg Pro Pro Lys
        290                 295                 300

Pro Pro Ala Thr Thr Thr Gly Ala Leu Asn His Asp Ala Lys Glu Leu
305                 310                 315                 320

His Met Phe Val Trp Ser Ser Ser Ala Ser Pro Val Ser Glu Val Ser
                325                 330                 335

Gly Leu Pro Val Phe Ser Gly Gly Gly Gly Gly Ala Leu Asp Val
                340                 345                 350

Gly Ala Lys Glu Ile His Met Val Ile Pro Ala Asp Leu Pro Gln Asn
        355                 360                 365

Asn Gly Ser Gly Lys Glu His Glu Glu Tyr Gly Ala Val Ala Leu Gly
        370                 375                 380

Gly Gly Gly Gly Glu Asn Phe Ser Phe Gly Gly Lys Thr Val
385                 390                 395                 400

Asp Gly Ala Glu Ala Val Asp Glu Glu Ala Ala Leu Pro Asp Gly Leu
                405                 410                 415

Thr Lys Met Gly Ser Ser Ser Thr Ala Glu Leu His Pro Lys Val Val
                420                 425                 430

Asp Val Asp Gly Pro Asn Ala Gly Gly Gly Ala Ala Gly Ala Gly Gln
            435                 440                 445

Tyr Gln Met Pro Pro Ala Ser Val Met Thr Arg Leu Ile Leu Ile Met
        450                 455                 460

Val Trp Arg Lys Leu Ile Arg Asn Pro Asn Thr Tyr Ser Ser Leu Leu
465                 470                 475                 480

Gly Leu Ala Trp Ser Leu Val Ala Phe Arg Leu Phe Met Ala Leu Gln
                485                 490                 495

Pro Ser Ile Ile Ala Cys Gly Lys Ser Ala Ala Val Val Ser Met Ala
                500                 505                 510

Val Arg Phe Leu Ala Gly Pro Ala Val Met Ala Ala Ser Ile Ala
        515                 520                 525

Ile Gly Leu Arg Gly Thr Leu Leu His Val Ala Ile Val Gln Ala Ala
        530                 535                 540

Leu Pro Gln Gly Ile Val Pro Phe Val Phe Ala Lys Glu Tyr Asn Val
545                 550                 555                 560

His Pro Ala Ile Leu Ser Thr Ala Val Ile Phe Gly Met Leu Ile Ala
```

```
                    565                 570                 575
Leu Pro Ile Thr Leu Leu Tyr Tyr Ile Leu Leu Gly Leu
            580                 585

<210> SEQ ID NO 21
<211> LENGTH: 1618
<212> TYPE: DNA
<213> ORGANISM: Glycine max

<400> SEQUENCE: 21
gcacgaggat ctctgagcag ttcccagaca ctgccggtac cattgtctcc atccatgtcg      60
actctgatgt catgtctctt gacggacgac agcaccctct ggaaaccgat gcccaaatca     120
aagaggacgg caagctccac gtcactgtca gaaaatccaa cgcttccaga tccgacatct     180
tttctagaag gtcccagggc ttctcttcca ccacccctcg cccttccaat ctcaccaatg     240
ctgagattta ctctcttcag tcctctcgaa accctactcc acgtggctcc agtttcaacc     300
acaccgattt ctactccatg atggctgctg gtcgtaattc taactttggt gccaacgatg     360
tttatggcct tctgcttcc agaggaccaa ctcccagacc ttccaattac gacgaggatg     420
cttctaataa taacaatggg aagccgaggt accactaccc tgctgctgga acaggaacag     480
gaacaggaac aggaacggga acgggaacag ggcactaccc tgctcctaac cctggcatgt     540
tctctcccac tgcttctaaa aacgtcgcca agaagccaga cgatccaaat aaggaccttc     600
atatgttcgt ttggagttca agtgcttccc cggtttcgga tgtgtttggt ggtggacatg     660
aatatgatca taaagaactc aagttaactg tatctccagg aaaagtggag ggtaatatta     720
atagagacac tcaagaggag taccagccag agaaagatga atttagtttt ggaaacagag     780
ggattgagga tgagcatgaa ggtgagaaag ttggaaacgg aaatccaaaa acaatgcctc     840
cagcaagtgt aatgacgagg cttatttga tcatggtgtg gaggaaactt atcagaaacc     900
ccaacaccta ctccagccta atcggcctaa cttggtcact catttcattc aggtggaacg     960
taaaaatgcc agccataatt gccaagtcta tttcgatatt gtcagatgca gggcttggga    1020
tggccatgtt tagtcttggt ctgttcatgg ctttgcaacc gaggatcata gcatgtggaa    1080
attccacagc agcttttttct atggccgtga gattccttac aggtccagct gtcatggcag    1140
ctgcttccat tgctgttgga ctcaaaggcg ttctcttgca cgttgctatt gttcaggcag    1200
ctcttcctca aggaattgtc ccatttgtct tgccaagga atacaatgta catcctgata    1260
ttctcagtac gggtgttatt tttgggatgt tgattgcatt gcccattacg ctcgtgtact    1320
acatcttgct ggggttatga gtgaatgaga agatggagga tatgaagatt acatgtggca    1380
tggcatgcat gcaatctcgt ttgagactcc ttagagcacg acaacaaatg ttcaatgaaa    1440
tacaaaagca tcaccataat tgaataggag gaatcgatca acggatgagt tttcattttt    1500
cttcttcttt ttttttttaat gaattgtcct tgctcagtga aaatgtaaaa tcatgtttgt    1560
agctaattta taaaatggct atctcgttaa atttcaaatt aaaaaaaaaa aaaaaaa       1618

<210> SEQ ID NO 22
<211> LENGTH: 443
<212> TYPE: PRT
<213> ORGANISM: Glycine max

<400> SEQUENCE: 22

Ile Ser Glu Gln Phe Pro Asp Thr Ala Gly Thr Ile Val Ser Ile His
 1               5                  10                  15

Val Asp Ser Asp Val Met Ser Leu Asp Gly Arg Gln His Pro Leu Glu
            20                  25                  30
```

```
Thr Asp Ala Gln Ile Lys Glu Asp Gly Lys Leu His Val Thr Val Arg
        35                  40                  45
Lys Ser Asn Ala Ser Arg Ser Asp Ile Phe Ser Arg Arg Ser Gln Gly
        50                  55                  60
Phe Ser Ser Thr Thr Pro Arg Pro Ser Asn Leu Thr Asn Ala Glu Ile
65                  70                  75                  80
Tyr Ser Leu Gln Ser Ser Arg Asn Pro Thr Pro Arg Gly Ser Ser Phe
                85                  90                  95
Asn His Thr Asp Phe Tyr Ser Met Met Ala Ala Gly Arg Asn Ser Asn
            100                 105                 110
Phe Gly Ala Asn Asp Val Tyr Gly Leu Ser Ala Ser Arg Gly Pro Thr
            115                 120                 125
Pro Arg Pro Ser Asn Tyr Asp Glu Asp Ala Ser Asn Asn Asn Asn Gly
        130                 135                 140
Lys Pro Arg Tyr His Tyr Pro Ala Ala Gly Thr Gly Thr Gly Thr Gly
145                 150                 155                 160
Thr Gly Thr Gly Thr Gly Thr Gly His Tyr Pro Ala Pro Asn Pro Gly
                165                 170                 175
Met Phe Ser Pro Thr Ala Ser Lys Asn Val Ala Lys Lys Pro Asp Asp
            180                 185                 190
Pro Asn Lys Asp Leu His Met Phe Val Trp Ser Ser Ala Ser Pro
        195                 200                 205
Val Ser Asp Val Phe Gly Gly Gly His Glu Tyr Asp His Lys Glu Leu
        210                 215                 220
Lys Leu Thr Val Ser Pro Gly Lys Val Glu Gly Asn Ile Asn Arg Asp
225                 230                 235                 240
Thr Gln Glu Glu Tyr Gln Pro Glu Lys Asp Glu Phe Ser Phe Gly Asn
                245                 250                 255
Arg Gly Ile Glu Asp Glu His Glu Gly Glu Lys Val Gly Asn Gly Asn
            260                 265                 270
Pro Lys Thr Met Pro Pro Ala Ser Val Met Thr Arg Leu Ile Leu Ile
        275                 280                 285
Met Val Trp Arg Lys Leu Ile Arg Asn Pro Asn Thr Tyr Ser Ser Leu
        290                 295                 300
Ile Gly Leu Thr Trp Ser Leu Ile Ser Phe Arg Trp Asn Val Lys Met
305                 310                 315                 320
Pro Ala Ile Ile Ala Lys Ser Ile Ser Ile Leu Ser Asp Ala Gly Leu
                325                 330                 335
Gly Met Ala Met Phe Ser Leu Gly Leu Phe Met Ala Leu Gln Pro Arg
            340                 345                 350
Ile Ile Ala Cys Gly Asn Ser Thr Ala Ala Phe Ser Met Ala Val Arg
        355                 360                 365
Phe Leu Thr Gly Pro Ala Val Met Ala Ala Ser Ile Ala Val Gly
        370                 375                 380
Leu Lys Gly Val Leu Leu His Val Ala Ile Val Gln Ala Ala Leu Pro
385                 390                 395                 400
Gln Gly Ile Val Pro Phe Val Phe Ala Lys Glu Tyr Asn Val His Pro
                405                 410                 415
Asp Ile Leu Ser Thr Gly Val Ile Phe Gly Met Leu Ile Ala Leu Pro
            420                 425                 430
Ile Thr Leu Val Tyr Tyr Ile Leu Leu Gly Leu
        435                 440
```

```
<210> SEQ ID NO 23
<211> LENGTH: 531
<212> TYPE: DNA
<213> ORGANISM: Glycine max
<220> FEATURE:
<221> NAME/KEY: unsure
<222> LOCATION: (530)
<223> OTHER INFORMATION: n=a,c,g or t

<400> SEQUENCE: 23
tctgacactc cctcacttca tccttctaca cattcacatc ttctctgaaa caattacaaa      60
gtgagtgaaa gtagtgtcct agcactagta gtacagtaca gaaaactaga agagcaacca     120
aaattttcca attagcacta gtagtacagt acaaaaaact agaagagcaa ccaaaatttt     180
ccaattgaaa agaaataac aacgagaaca aatcttatc gtgagatcga ataactgaaa       240
aaaaaggaaa gaagaacaaa aatgataac gtggaaagac ctatacacgg tcctgaccgc      300
agtggtccct ctctacgtgg cgatgatcct ggcgtacggc tcggtccggt ggtggaaaga     360
tcttctcacc ggaccagtgc tccggcataa accgcttcgt ggcgatcttc gccgtgccgc     420
tcctctcctt ccacttcatc tccaccaaca ccctacgc catgaacttc cgcttcatcc       480
gccgccggac acctccaaga agatcatcat gctcttcgcc cttgcaaccn g              531

<210> SEQ ID NO 24
<211> LENGTH: 90
<212> TYPE: PRT
<213> ORGANISM: Glycine max
<220> FEATURE:
<221> NAME/KEY: UNSURE
<222> LOCATION: (33)
<223> OTHER INFORMATION: Xaa = ANY AMINO ACID
<220> FEATURE:
<221> NAME/KEY: UNSURE
<222> LOCATION: (78)
<223> OTHER INFORMATION: Xaa = ANY AMINO ACID

<400> SEQUENCE: 24

Met Ile Thr Trp Lys Asp Leu Tyr Thr Val Leu Thr Ala Val Val Pro
 1               5                  10                  15

Leu Tyr Val Ala Met Ile Leu Ala Tyr Gly Ser Val Arg Trp Trp Lys
            20                  25                  30

Xaa Ile Phe Ser Pro Asp Gln Cys Ser Gly Ile Asn Arg Phe Val Ala
        35                  40                  45

Ile Phe Ala Val Pro Leu Leu Ser Phe His Phe Ile Ser Thr Asn Asn
    50                  55                  60

Pro Tyr Ala Met Asn Phe Arg Phe Ile Arg Arg Arg Thr Xaa Thr Ser
 65                  70                  75                  80

Lys Lys Ile Ile Met Leu Phe Ala Leu Ala
            85                  90

<210> SEQ ID NO 25
<211> LENGTH: 2101
<212> TYPE: DNA
<213> ORGANISM: Glycine max

<400> SEQUENCE: 25
ctttctctga cactccctca cttcatcctt ctacacattc acatcttctc tgaaacaatt      60
acaaagtgag tgaaagtagt gtcctagcac tagtagtaca gtacagaaaa ctagaagagc     120
aaccaaaatt ttccaattag cactagtagt acagtacaaa aaactagaag agcaaccaaa     180
attttccaat tgaaaagaa ataacaacga gaacaaaatc ttatcgtgag atcgaataac      240
tgaaaaaaaa ggaaagaaga acaaaaaatg ataacgtgga aagacctata cacggtcctg     300
```

```
accgcagtgg tccctctcta cgtggcgatg atcctggcgt acggctcggt ccggtggtgg      360
aagatcttct caccggacca gtgctccggc ataaaccgct tcgtggcgat cttcgccgtg      420
ccgctcctct ccttccactt catctccacc aacaacccct acgccatgaa cttccgcttc      480
atcgccgccg acaccctcca agagatcatc atgctcttcg cccttgccat ctggaccaac      540
ctcaccaaaa ccggttccct agagtggatg attaccatct tctccctctc aacccttccc      600
aataccttag tcatgggaat tccactccta atcgccatgt acggcgacta ctccggctcg      660
ctcatggttc aggtcgtggt ccttcagtgc atcatatggt acaccttgtt gctcttctta      720
ttcgaatacc gcgccgcgaa atcctaatc atggaacagt tccctgaaac cgctgcctcc       780
atcgtgtcgt ttaaagtcga ctccgacgtc gtttcgctcg acgggaggga cttcttggag      840
accgacgccg aagtcggtga cgatgggaag cttcatgtca ccgttagaaa gtcgaacgcc      900
tcgcgtaggt cgtttatgat gacgccgagg ccttctaatc tcactggggc ggagatttac      960
agcctcagct cgtctcgtaa cccaacacca cgtggctcaa actttaacca tgcggatttc     1020
ttctccatga tggggtacca gcctcgccac tccaatttca cggccaatga tttgttctcc     1080
tcgcgtggac ccactccgag gccttctaat ttcgaagaac cctcaatgcc tcaggcggtg     1140
acggtagctt ctcctcggtt cgggttctac ccgtcccaaa ccgtgccagc ttcgtacccg     1200
ccgcccaacc cggattttc ctccgctact aaaaacttga agaatcaaag tcagaatcag       1260
aatccgaacc agagccagag ccagaattcg caggctccgg cgaagggtgc ccacgatgcg     1320
aaggagctcc acatgtttgt gtggagctcc agtgcctccc cgatgtcgga gaatgccgga     1380
ctcaacgtct ttagcagcac agacctcgga acctccgaac aacctgacca gggtgctaaa     1440
gagattagga tgttggtggc tgataataat gcacacttac gaaatggtga agccaacaac     1500
aaaggtggtt tggaggcagt acttggtgtg gaagacttca gtttctggt gaatggcgaa       1560
gaacaagttg gggaagaaaa agaagggctc aacaatgggc ttaacaagtt gggctcaagc     1620
tccacggtgg agctccaacc aaaagccacc gtagccggcg aggcttccgc cggaaaacac     1680
atgcctccgg caaatgtcat gactcgtctc atactcatca tggtgtggag aaagcttatc     1740
cgcaatccca acacatactc tagcctaatt ggtgtagtat ggtccctcgt tgcattcagg     1800
tggcacgtgc atatgcccaa aataatagag aaatcaattt ccatactgtc tgatgccggt     1860
cttggaatgg ctatgttcag cttaggtgac tggtcgcaaa tccattctcc aaattcatac     1920
tctcgcgaaa taatttcatt cttttatcca aaaacaattt cgcttccctc tttcccatag     1980
atcattattt tattggctcc aattgttagt gtaaatgtgg atttccttat actaagaaaa     2040
taaaatgcat gtgtttaatt atctatttat ttatttctga cccaaaaaaa aaaaaaaaa      2100
a                                                                     2101
```

<210> SEQ ID NO 26
<211> LENGTH: 540
<212> TYPE: PRT
<213> ORGANISM: Glycine max

<400> SEQUENCE: 26

```
Met Ile Thr Trp Lys Asp Leu Tyr Thr Val Leu Thr Ala Val Val Pro
  1               5                  10                  15

Leu Tyr Val Ala Met Ile Leu Ala Tyr Gly Ser Val Arg Trp Trp Lys
             20                  25                  30

Ile Phe Ser Pro Asp Gln Cys Ser Gly Ile Asn Arg Phe Val Ala Ile
         35                  40                  45
```

-continued

```
Phe Ala Val Pro Leu Leu Ser Phe His Phe Ile Ser Thr Asn Asn Pro
         50                   55                  60

Tyr Ala Met Asn Phe Arg Phe Ile Ala Ala Asp Thr Leu Gln Lys Ile
 65                   70                  75                  80

Ile Met Leu Phe Ala Leu Ala Ile Trp Thr Asn Leu Thr Lys Thr Gly
                 85                  90                  95

Ser Leu Glu Trp Met Ile Thr Ile Phe Ser Leu Ser Thr Leu Pro Asn
                100                 105                 110

Thr Leu Val Met Gly Ile Pro Leu Leu Ile Ala Met Tyr Gly Asp Tyr
            115                 120                 125

Ser Gly Ser Leu Met Val Gln Val Val Leu Gln Cys Ile Ile Trp
        130                 135                 140

Tyr Thr Leu Leu Leu Phe Leu Phe Glu Tyr Arg Ala Ala Lys Ile Leu
145                 150                 155                 160

Ile Met Glu Gln Phe Pro Glu Thr Ala Ala Ser Ile Val Ser Phe Lys
                165                 170                 175

Val Asp Ser Asp Val Val Ser Leu Asp Gly Arg Asp Phe Leu Glu Thr
            180                 185                 190

Asp Ala Glu Val Gly Asp Asp Gly Lys Leu His Val Thr Val Arg Lys
            195                 200                 205

Ser Asn Ala Ser Arg Arg Ser Phe Met Met Thr Pro Arg Pro Ser Asn
        210                 215                 220

Leu Thr Gly Ala Glu Ile Tyr Ser Leu Ser Ser Arg Asn Pro Thr
225                 230                 235                 240

Pro Arg Gly Ser Asn Phe Asn His Ala Asp Phe Phe Ser Met Met Gly
                245                 250                 255

Tyr Gln Pro Arg His Ser Asn Phe Thr Ala Asn Asp Leu Phe Ser Ser
                260                 265                 270

Arg Gly Pro Thr Pro Arg Pro Ser Asn Phe Glu Glu Pro Ser Met Pro
            275                 280                 285

Gln Ala Val Thr Val Ala Ser Pro Arg Phe Gly Phe Tyr Pro Ser Gln
        290                 295                 300

Thr Val Pro Ala Ser Tyr Pro Pro Asn Pro Asp Phe Ser Ser Ala
305                 310                 315                 320

Thr Lys Asn Leu Lys Asn Gln Ser Gln Asn Gln Asn Pro Asn Gln Ser
                325                 330                 335

Gln Ser Gln Asn Ser Gln Ala Pro Ala Lys Gly Ala His Asp Ala Lys
            340                 345                 350

Glu Leu His Met Phe Val Trp Ser Ser Ala Ser Pro Met Ser Glu
        355                 360                 365

Asn Ala Gly Leu Asn Val Phe Ser Ser Thr Asp Leu Gly Thr Ser Glu
370                 375                 380

Gln Pro Asp Gln Gly Ala Lys Glu Ile Arg Met Leu Val Ala Asp Asn
385                 390                 395                 400

Asn Ala His Leu Arg Asn Gly Glu Ala Asn Asn Lys Gly Gly Leu Glu
                405                 410                 415

Ala Val Leu Gly Val Glu Asp Phe Lys Phe Leu Val Asn Gly Glu Glu
            420                 425                 430

Gln Val Gly Glu Glu Lys Glu Gly Leu Asn Asn Gly Leu Asn Lys Leu
        435                 440                 445

Gly Ser Ser Ser Thr Val Glu Leu Gln Pro Lys Ala Thr Val Ala Gly
    450                 455                 460

Glu Ala Ser Ala Gly Lys His Met Pro Pro Ala Asn Val Met Thr Arg
465                 470                 475                 480
```

```
Leu Ile Leu Ile Met Val Trp Arg Lys Leu Ile Arg Asn Pro Asn Thr
                485                 490                 495

Tyr Ser Ser Leu Ile Gly Val Val Trp Ser Leu Val Ala Phe Arg Trp
            500                 505                 510

His Val His Met Pro Lys Ile Ile Glu Lys Ser Ile Ser Ile Leu Ser
            515                 520                 525

Asp Ala Gly Leu Gly Met Ala Met Phe Ser Leu Gly
            530                 535             540

<210> SEQ ID NO 27
<211> LENGTH: 525
<212> TYPE: DNA
<213> ORGANISM: Glycine max

<400> SEQUENCE: 27
ccccactctg ccttgtgctt tggagactgc aagtgcaacc ttgcttgcag ctctcaaagc    60
tgaaaaaata tttgctgtat tctctgctgc acattagcac cattcactca ctcactgccc   120
caaaaccaca tgctcttcca catccctata aaaatctttt caatcttca taatcatcat    180 catcaccacc aactccaact caaactctcc aaaacctgcc acttcaacct tcctatatat   240
tccttccctc actctcttct gcttctatca tctttctgag aggcttgttg acacacaaaa   300
aatgatcacc ttaacagact tctaccatgt gatgactgca atggtgccac tctatgtggc   360
catgatacta gcctatggct cagtgaagtg gtggaagatt ttctcccctg ataatgctct   420
ggcatcaacc gttttgtggc actctttgca gtgcctcttc tctcctttca cttcatagcc   480
tcaaacaacc ctttatgaga tgaacctgaa ggtcctaact ggctg                   525

<210> SEQ ID NO 28
<211> LENGTH: 64
<212> TYPE: PRT
<213> ORGANISM: Glycine max
<220> FEATURE:
<221> NAME/KEY: UNSURE
<222> LOCATION: (38)
<223> OTHER INFORMATION: Xaa = ANY AMINO ACID

<400> SEQUENCE: 28

Met Ile Thr Leu Thr Asp Phe Tyr His Val Met Thr Ala Met Val Pro
  1               5                  10                  15

Leu Tyr Val Ala Met Ile Leu Ala Tyr Gly Ser Val Lys Trp Trp Lys
                20                  25                  30

Ile Phe Ser Pro Asp Xaa Cys Ser Gly Ile Asn Arg Phe Val Ala Leu
                35                  40                  45

Phe Ala Val Pro Leu Leu Ser Phe His Phe Ile Ala Ser Asn Asn Pro
        50                  55                  60

<210> SEQ ID NO 29
<211> LENGTH: 2549
<212> TYPE: DNA
<213> ORGANISM: Glycine max

<400> SEQUENCE: 29
gcacgagccc cactctgcct tgtgctttgg agactgcaag tgcaaccttg cttgcagctc    60
tcaaagctga aaaatatttt gctgtattct ctgctgcaca ttagcaccat tcactcactc   120
actgccccaa aaccacatgc tcttccacat ccctatataa aatcttttca atcttcataa   180
tcatcatcat caccaccaac tccaactcaa actctccaaa acctgccact tcaaccttcc   240
tatatattcc ttccctcact ctcttctgct tctatcatct ttctgagagg cttgttgaca   300
```

```
cacaaaaaat gatcacctta acagacttct accatgtgat gactgcaatg gtgccactct    360
atgtggccat gatactagcc tatggctcag tgaagtggtg gaagattttc tccctgatc     420 aatgctctgg catcaaccgt tttgtggcac tctttgcagt gcctcttctc tccttccact    480
tcatagcctc caacaaccct tatgagatga acctgaggtt cctagctgct gacacccttc    540
aaaagatcat aatactagtc ctccttgcag tttggagcaa catcaccaaa aggggttgtt    600
tggaatgggc cataaccttg ttctctctct ccaccctccc aaacactttg gttatgggca    660
tccctttgct caagggatg tatggtgact tctcagggag cctcatggtg caaattgtgg     720
tcctccagtg catcatttgg tacaccttga tgctcttctt gtttgagttt agaggtgcca    780
gaatgctcat ctctgagcag ttccctgaca ctgctgcctc cattgtctcc atccatgtgg    840
actctgatgt catgtcattg gatggaagac aaccacttga gactgaagct gagatcaagg    900
aagatggtaa actccatgtc actgtgagga aatccaatgc ttcaagatca gacatcttct    960
ctagaaggtc tcagggtctc tcttccacca ctccacgccc ttccaacctt accaatgctg   1020
agatatactc tttgcaatcc tctaggaacc ctacgccgag aggctctagt ttcaaccaca   1080
ctgatttcta ctccatgatg gctgctggtg gcaggaactc aaactttggt gcctctgatg   1140
tttatggcct ttcagcttca agagggccaa ctccaaggcc ttctaactat gatgaagatg   1200
gtgggaagcc aaagtttcat taccatgctg ctggtggaac tggcactac cctgcaccaa    1260 accctggcat gttctctccc tctaatgggt ccaaaagtgt tgctgctaat gctaatgcca   1320
agaggcctaa tgggcaggct cagctgaagc ctgaggatgg aataggac cttcatatgt      1380 ttgtttggag ttcaagtgct tcaccagttt ctgatgtgtt tggtgcccat gagtatggag   1440
gaggtcatga tcagaaagaa gtcaaattga atgtatctcc aggaaaagtg gagaataatc   1500
atagagacac tcaagaagac tacctagaga aagatgagtt cagctttggg aatagagaaa   1560
tggacaggga gatgaatcag cttgaaggtg agaaggttgg agatgggaaa ccaaaaacca   1620
tgcctccagc aagtgtgatg acaaggctta tattgattat ggtgtggaga aaactcatca   1680
gaaaccccaa cacctactct agcctaattg gtctcacttg gtctcttgtt tcattcaagt   1740
ggaatgttga gatgcctgcc ataatagcaa agtctatctc catattgtca gacgcagggc   1800
ttggcatggc catgttcagt cttggtctct tcatggcttt gcaaccgagg gtcatagcat   1860
gtggaaattc cacagcagct tttgccatgg ctgtgagatt ccttacaggt ccagctgtca   1920 tgcagctgc ttccattgct gttggactca aaggtgttct cctacacgtt gccattgttc     1980
aggcagctct tccccaagga attgtcccat tgtctttgc taaggaatat aatgtacatc     2040
ctgatattct cagcacagct gttattttg ggatgctgat tgctttgccc ataactctag     2100
tgtactacat cttgttgggg ttgtgaatga agaaatgat ggatgataca gaagattcac      2160
gtgtggcatc catgcaaagc ttggttgagg ttgttgagaa tgagagaaaa aaaaggtcat   2220
aaagcaacaa tagaaaagaa gcatcacgag aatttggata ggaagaagaa ccccaggatc   2280 agttttttttt atttatttgt tttctttttc tttttgaat gaattgccct ttcttagtga    2340
aaattaatgt aaaatcatga tgtagctaat ttacaaaatg attatctcgt taaaattta    2400 tattataatg acctcggatt ccatgtcact catcaattga aggataagaa agcatgagaa   2460
acttagttga tgaaaaaaaa aaaaaaaaaa aaaaaaaaaa aaaaaaaaaa aaaaaaaaaa   2520
aaaaaaaaaa aaaaaaaaaa aaaaaaaaa                                    2549
```

<210> SEQ ID NO 30
<211> LENGTH: 605

<212> TYPE: PRT
<213> ORGANISM: Glycine max

<400> SEQUENCE: 30

```
Met Ile Thr Leu Thr Asp Phe Tyr His Val Met Thr Ala Met Val Pro
  1               5                  10                  15

Leu Tyr Val Ala Met Ile Leu Ala Tyr Gly Ser Val Lys Trp Trp Lys
             20                  25                  30

Ile Phe Ser Pro Asp Gln Cys Ser Gly Ile Asn Arg Phe Val Ala Leu
         35                  40                  45

Phe Ala Val Pro Leu Leu Ser Phe His Phe Ile Ala Ser Asn Asn Pro
     50                  55                  60

Tyr Glu Met Asn Leu Arg Phe Leu Ala Ala Asp Thr Leu Gln Lys Ile
 65                  70                  75                  80

Ile Ile Leu Val Leu Leu Ala Val Trp Ser Asn Ile Thr Lys Arg Gly
                 85                  90                  95

Cys Leu Glu Trp Ala Ile Thr Leu Phe Ser Leu Ser Thr Leu Pro Asn
            100                 105                 110

Thr Leu Val Met Gly Ile Pro Leu Leu Lys Gly Met Tyr Gly Asp Phe
        115                 120                 125

Ser Gly Ser Leu Met Val Gln Ile Val Val Leu Gln Cys Ile Ile Trp
    130                 135                 140

Tyr Thr Leu Met Leu Phe Leu Phe Glu Phe Arg Gly Ala Arg Met Leu
145                 150                 155                 160

Ile Ser Glu Gln Phe Pro Asp Thr Ala Ala Ser Ile Val Ser Ile His
                165                 170                 175

Val Asp Ser Asp Val Met Ser Leu Asp Gly Arg Gln Pro Leu Glu Thr
            180                 185                 190

Glu Ala Glu Ile Lys Glu Asp Gly Lys Leu His Val Thr Val Arg Lys
        195                 200                 205

Ser Asn Ala Ser Arg Ser Asp Ile Phe Ser Arg Ser Gln Gly Leu
    210                 215                 220

Ser Ser Thr Thr Pro Arg Pro Ser Asn Leu Thr Asn Ala Glu Ile Tyr
225                 230                 235                 240

Ser Leu Gln Ser Ser Arg Asn Pro Thr Pro Arg Gly Ser Ser Phe Asn
                245                 250                 255

His Thr Asp Phe Tyr Ser Met Met Ala Ala Gly Gly Arg Asn Ser Asn
            260                 265                 270

Phe Gly Ala Ser Asp Val Tyr Gly Leu Ser Ala Ser Arg Gly Pro Thr
        275                 280                 285

Pro Arg Pro Ser Asn Tyr Asp Glu Asp Gly Gly Lys Pro Lys Phe His
    290                 295                 300

Tyr His Ala Ala Gly Gly Thr Gly His Tyr Pro Ala Pro Asn Pro Gly
305                 310                 315                 320

Met Phe Ser Pro Ser Asn Gly Ser Lys Ser Val Ala Ala Asn Ala Asn
                325                 330                 335

Ala Lys Arg Pro Asn Gly Gln Ala Gln Leu Lys Pro Glu Asp Gly Asn
            340                 345                 350

Arg Asp Leu His Met Phe Val Trp Ser Ser Ser Ala Ser Pro Val Ser
        355                 360                 365

Asp Val Phe Gly Ala His Glu Tyr Gly Gly His Asp Gln Lys Glu
    370                 375                 380

Val Lys Leu Asn Val Ser Pro Gly Lys Val Glu Asn Asn His Arg Asp
385                 390                 395                 400
```

```
Thr Gln Glu Asp Tyr Leu Glu Lys Asp Glu Phe Ser Phe Gly Asn Arg
            405                 410                 415
Glu Met Asp Arg Glu Met Asn Gln Leu Glu Gly Glu Lys Val Gly Asp
        420                 425                 430
Gly Lys Pro Lys Thr Met Pro Pro Ala Ser Val Met Thr Arg Leu Ile
435                 440                 445
Leu Ile Met Val Trp Arg Lys Leu Ile Arg Asn Pro Asn Thr Tyr Ser
    450                 455                 460
Ser Leu Ile Gly Leu Thr Trp Ser Leu Val Ser Phe Lys Trp Asn Val
465                 470                 475                 480
Glu Met Pro Ala Ile Ile Ala Lys Ser Ile Ser Ile Leu Ser Asp Ala
                485                 490                 495
Gly Leu Gly Met Ala Met Phe Ser Leu Gly Leu Phe Met Ala Leu Gln
            500                 505                 510
Pro Arg Val Ile Ala Cys Gly Asn Ser Thr Ala Ala Phe Ala Met Ala
        515                 520                 525
Val Arg Phe Leu Thr Gly Pro Ala Val Met Ala Ala Ser Ile Ala
    530                 535                 540
Val Gly Leu Lys Gly Val Leu His Val Ala Ile Val Gln Ala Ala
545                 550                 555                 560
Leu Pro Gln Gly Ile Val Pro Phe Val Phe Ala Lys Glu Tyr Asn Val
                565                 570                 575
His Pro Asp Ile Leu Ser Thr Ala Val Ile Phe Gly Met Leu Ile Ala
            580                 585                 590
Leu Pro Ile Thr Leu Val Tyr Tyr Ile Leu Leu Gly Leu
        595                 600                 605
```

```
<210> SEQ ID NO 31
<211> LENGTH: 419
<212> TYPE: DNA
<213> ORGANISM: Glycine max
<220> FEATURE:
<221> NAME/KEY: unsure
<222> LOCATION: (237)
<223> OTHER INFORMATION: n=a,c,g or t
<220> FEATURE:
<221> NAME/KEY: unsure
<222> LOCATION: (250)
<223> OTHER INFORMATION: n=a,c,g or t
<220> FEATURE:
<221> NAME/KEY: unsure
<222> LOCATION: (347)
<223> OTHER INFORMATION: n=a,c,g or t

<400> SEQUENCE: 31
ctttatcgtg agagttttgc ctttatttct cagccatgtt tccttctttt ccagcttaaa      60
ccgctaccct acaaaacctt tcacaattct ctttcttcct agctatctct ttctttctgt     120
ctacattgac ctagctagct acaaaccctg cattaaccat gatcactggt aaggatattt     180
atgatgtttt cgcggctatt gtgcccctct acgttgctat gatattaagc atacggntca     240
gttcggtggn ggaaaatttt cacacctgat caatgttctg cataaaccg cttcgttgct      300 gtgttcgcag ttccacttct ttctttccac ttcatctcct ccaatgnccc ttatgctatg     360
aactaccact tcatagcagc tgattgtctt caaaagttg tcattttggg gggctcccc      419

<210> SEQ ID NO 32
<211> LENGTH: 84
<212> TYPE: PRT
<213> ORGANISM: Glycine max
<220> FEATURE:
<221> NAME/KEY: UNSURE
```

<222> LOCATION: (25)
<223> OTHER INFORMATION: Xaa = ANY AMINO ACID
<220> FEATURE:
<221> NAME/KEY: UNSURE
<222> LOCATION: (32)
<223> OTHER INFORMATION: Xaa = ANY AMINO ACID
<220> FEATURE:
<221> NAME/KEY: UNSURE
<222> LOCATION: (64)
<223> OTHER INFORMATION: Xaa = ANY AMINO ACID

<400> SEQUENCE: 32

Met Ile Thr Gly Lys Asp Ile Tyr Asp Val Phe Ala Ala Ile Val Pro
 1               5                  10                  15

Leu Tyr Val Ala Met Ile Leu Ser Xaa Tyr Gly Ser Val Arg Trp Xaa
            20                  25                  30

Lys Ile Phe Thr Pro Asp Gln Cys Ser Gly Ile Asn Arg Phe Val Ala
        35                  40                  45

Val Phe Ala Val Pro Leu Leu Ser Phe His Phe Ile Ser Ser Asn Xaa
    50                  55                  60

Pro Tyr Ala Met Asn Tyr His Phe Ile Ala Ala Asp Cys Leu Gln Lys
65                  70                  75                  80

Val Val Ile Leu

<210> SEQ ID NO 33
<211> LENGTH: 2324
<212> TYPE: DNA
<213> ORGANISM: Glycine max

<400> SEQUENCE: 33
gcacgagctt tatcgtgaga gttttgcctt tatttctcag ccatgtttcc ttcttttcca      60
gcttaaaccg ctaccctaca aaacctttca caattctctt tcttcctagc tatctctttc     120
tttctgtcta cattgaccta gctagctaca aaccctgcat taaccatgat cactggtaag     180
gatatttatg atgttttcgc ggctattgtg cccctctacg ttgctatgat attagcatac     240
ggctcagttc ggtggtggaa attttcaca cctgatcaat gttctggcat aaaccgcttc      300
gttgctgtgt tcgcagttcc acttctttct ttccacttca tctcctccaa tgacccttat     360
gctatgaact accacttcat agcagctgat tgtcttcaaa agttgtcat tttgggtgct      420
ctctttctat ggaacacctt cacaaaacat ggtagcctag actggacaat caccctcttc     480
tcactttcaa cccttccaaa cacacttgtc atggggatcc ctctattgaa ggccatgtat     540
ggagacttct cagggagcct catggtccaa attgtggtgt tgcaaagtgt gatatggtat     600
accctcatgc tgttcatgtt tgaatataga ggtgcaaaac tcctcatcac agaacagttc     660
cctgagactg caggctccat aacttccttc agggttgact cagatgttgt ctcactcaat     720
ggtagagagc cacttcaaac agatgctgag ataggagaag atggaaaact tcatgtggtt     780
gttaaaagat cagcagcttc ttccatgata tcttcattca acaagtctca tttaacttcc     840
atgacaccaa gagcatctaa cctcactggg gttgagatct attctgttca gtcatcaaga     900
gaaccaaccc caagaggttc gagtttcaac caaacggatt tctatgccat gttcgcaagc     960
aaggcaccga gtccaaaaca tggctacaca aacagtttcc agagtaataa tggtggtatt    1020
ggtgacgttt actcgttgca gtcttcaaaa ggggcaacgc caaggacttc taattttgaa    1080
gaggagatgt tgaagatgca caagaagaga ggagggagga gcatgagtgg cgagttgttt    1140
aatgggggtt tggtttcttc taattacccg ccaccgaatc caatgttttc agggtctacg    1200
agtgctgctg gtggccccaa gaagaaagat agcagtggtg gcggtggtgc tgtagcacct    1260

-continued

```
aacaaggagt tacacatgtt tgtttggagt tcaagtgcat cacctgtttc tgagggaat    1320 ttgaggcatg cagttaatag agctgcctct actgactttg gaactgtcga tccttctaag    1380
gctgttccac acgaaactgt tgcctcaaaa gctgttcacg aattgattga gaacatgagc    1440
cctggtcgta gagggagtgg agagaggag cctgaaatgg atgaaggagc caaaattccc     1500
gcaagtggat ctccatacac ttgccagaag aaggtggaca tggaagatgg caatgcaaac    1560
aaaaaccaac agatgccacc tgcaagtgtc atgacaagac ttattctcat catggtttgg    1620
aggaaactca taagaaatcc taatacttac tccagtcttt tgggactcac atggtctctc    1680
atatcattta ggtggcacat tgaaatgcca actattgtaa aaggttccat ctcaatactg    1740
tctgatgctg gtctaggaat ggccatgttc agtctaggtc tattcatggc attacaaccg    1800
aagatcattg cctgtggaaa atctgtggca gcatttcaa tggctgttag gttcttgaca     1860
ggtccagctg tgattgctgc aacctcaata ggcatcggac tccgtggagt tcttttgcat    1920
gttgcaattg tccaggctgc tcttccccaa ggtatcgttc cctttgtgtt tgccaaagaa    1980
tacaatctcc atgcagatat acttagcact gcggttatat ttgggatgct aattgcattg    2040
cccataacca tactctacta cgtgctgctt ggagtttaat ttgtcttggg agacaaaagc    2100
aatagaaaaa gaagtatatg ttgctataac tgtacgtact atgtaaaccc aatgtcacgc    2160
tcaagcgggg tggatgaagg gaaatgtaga agatattgga ttttagatgt tagagggaaa    2220
gagaaattat atatagtata cggtagaatg ctatatatat taattattta tgattcatat    2280
gaaaattttg gtttgattcg ttccacaaaa aaaaaaaaaa aaaa                     2324
```

<210> SEQ ID NO 34
<211> LENGTH: 637
<212> TYPE: PRT
<213> ORGANISM: Glycine max

<400> SEQUENCE: 34

```
Met Ile Thr Gly Lys Asp Ile Tyr Asp Val Phe Ala Ala Ile Val Pro
  1               5                  10                  15

Leu Tyr Val Ala Met Ile Leu Ala Tyr Gly Ser Val Arg Trp Trp Lys
             20                  25                  30

Ile Phe Thr Pro Asp Gln Cys Ser Gly Ile Asn Arg Phe Val Ala Val
         35                  40                  45

Phe Ala Val Pro Leu Leu Ser Phe His Phe Ile Ser Ser Asn Asp Pro
     50                  55                  60

Tyr Ala Met Asn Tyr His Phe Ile Ala Ala Asp Cys Leu Gln Lys Val
 65                  70                  75                  80

Val Ile Leu Gly Ala Leu Phe Leu Trp Asn Thr Phe Thr Lys His Gly
                 85                  90                  95

Ser Leu Asp Trp Thr Ile Thr Leu Phe Ser Leu Ser Thr Leu Pro Asn
            100                 105                 110

Thr Leu Val Met Gly Ile Pro Leu Leu Lys Ala Met Tyr Gly Asp Phe
        115                 120                 125

Ser Gly Ser Leu Met Val Gln Ile Val Val Leu Gln Ser Val Ile Trp
    130                 135                 140

Tyr Thr Leu Met Leu Phe Met Phe Glu Tyr Arg Gly Ala Lys Leu Leu
145                 150                 155                 160

Ile Thr Glu Gln Phe Pro Glu Thr Ala Gly Ser Ile Thr Ser Phe Arg
                165                 170                 175

Val Asp Ser Asp Val Val Ser Leu Asn Gly Arg Glu Pro Leu Gln Thr
            180                 185                 190
```

```
Asp Ala Glu Ile Gly Glu Asp Gly Lys Leu His Val Val Lys Arg
            195                 200                 205

Ser Ala Ala Ser Ser Met Ile Ser Ser Phe Asn Lys Ser His Leu Thr
    210                 215                 220

Ser Met Thr Pro Arg Ala Ser Asn Leu Thr Gly Val Glu Ile Tyr Ser
225                 230                 235                 240

Val Gln Ser Ser Arg Glu Pro Thr Pro Arg Gly Ser Ser Phe Asn Gln
                245                 250                 255

Thr Asp Phe Tyr Ala Met Phe Ala Ser Lys Ala Pro Ser Pro Lys His
                260                 265                 270

Gly Tyr Thr Asn Ser Phe Gln Ser Asn Gly Ile Gly Asp Val
                275                 280                 285

Tyr Ser Leu Gln Ser Ser Lys Gly Ala Thr Pro Arg Thr Ser Asn Phe
    290                 295                 300

Glu Glu Glu Met Leu Lys Met His Lys Lys Arg Gly Arg Ser Met
305                 310                 315                 320

Ser Gly Glu Leu Phe Asn Gly Gly Leu Val Ser Ser Asn Tyr Pro Pro
                325                 330                 335

Pro Asn Pro Met Phe Ser Gly Ser Thr Ser Ala Ala Gly Gly Pro Lys
                340                 345                 350

Lys Lys Asp Ser Ser Gly Gly Gly Ala Val Ala Pro Asn Lys Glu
            355                 360                 365

Leu His Met Phe Val Trp Ser Ser Ala Ser Pro Val Ser Glu Gly
    370                 375                 380

Asn Leu Arg His Ala Val Asn Arg Ala Ala Ser Thr Asp Phe Gly Thr
385                 390                 395                 400

Val Asp Pro Ser Lys Ala Val Pro His Glu Thr Val Ala Ser Lys Ala
                405                 410                 415

Val His Glu Leu Ile Glu Asn Met Ser Pro Gly Arg Arg Gly Ser Gly
                420                 425                 430

Glu Arg Glu Pro Glu Met Asp Glu Gly Ala Lys Ile Pro Ala Ser Gly
            435                 440                 445

Ser Pro Tyr Thr Cys Gln Lys Lys Val Asp Met Glu Asp Gly Asn Ala
    450                 455                 460

Asn Lys Asn Gln Gln Met Pro Pro Ala Ser Val Met Thr Arg Leu Ile
465                 470                 475                 480

Leu Ile Met Val Trp Arg Lys Leu Ile Arg Asn Pro Asn Thr Tyr Ser
                485                 490                 495

Ser Leu Leu Gly Leu Thr Trp Ser Leu Ile Ser Phe Arg Trp His Ile
            500                 505                 510

Glu Met Pro Thr Ile Val Lys Gly Ser Ile Ser Ile Leu Ser Asp Ala
    515                 520                 525

Gly Leu Gly Met Ala Met Phe Ser Leu Gly Leu Phe Met Ala Leu Gln
530                 535                 540

Pro Lys Ile Ile Ala Cys Gly Lys Ser Val Ala Ala Phe Ser Met Ala
545                 550                 555                 560

Val Arg Phe Leu Thr Gly Pro Ala Val Ile Ala Ala Thr Ser Ile Gly
                565                 570                 575

Ile Gly Leu Arg Gly Val Leu Leu His Val Ala Ile Val Gln Ala Ala
            580                 585                 590

Leu Pro Gln Gly Ile Val Pro Phe Val Phe Ala Lys Glu Tyr Asn Leu
    595                 600                 605

His Ala Asp Ile Leu Ser Thr Ala Val Ile Phe Gly Met Leu Ile Ala
                610                 615                 620
```

```
Leu Pro Ile Thr Ile Leu Tyr Tyr Val Leu Leu Gly Val
625                 630                 635

<210> SEQ ID NO 35
<211> LENGTH: 473
<212> TYPE: DNA
<213> ORGANISM: Triticum aestivum
<220> FEATURE:
<221> NAME/KEY: unsure
<222> LOCATION: (22)
<223> OTHER INFORMATION: n=a,c,g or t
<220> FEATURE:
<221> NAME/KEY: unsure
<222> LOCATION: (46)
<223> OTHER INFORMATION: n=a,c,g or t
<220> FEATURE:
<221> NAME/KEY: unsure
<222> LOCATION: (58)
<223> OTHER INFORMATION: n=a,c,g or t
<220> FEATURE:
<221> NAME/KEY: unsure
<222> LOCATION: (61)
<223> OTHER INFORMATION: n=a,c,g or t
<220> FEATURE:
<221> NAME/KEY: unsure
<222> LOCATION: (91)
<223> OTHER INFORMATION: n=a,c,g or t
<220> FEATURE:
<221> NAME/KEY: unsure
<222> LOCATION: (98)
<223> OTHER INFORMATION: n=a,c,g or t
<220> FEATURE:
<221> NAME/KEY: unsure
<222> LOCATION: (101)
<223> OTHER INFORMATION: n=a,c,g or t
<220> FEATURE:
<221> NAME/KEY: unsure
<222> LOCATION: (122)
<223> OTHER INFORMATION: n=a,c,g or t
<220> FEATURE:
<221> NAME/KEY: unsure
<222> LOCATION: (177)
<223> OTHER INFORMATION: n=a,c,g or t
<220> FEATURE:
<221> NAME/KEY: unsure
<222> LOCATION: (201)
<223> OTHER INFORMATION: n=a,c,g or t
<220> FEATURE:
<221> NAME/KEY: unsure
<222> LOCATION: (297)
<223> OTHER INFORMATION: n=a,c,g or t
<220> FEATURE:
<221> NAME/KEY: unsure
<222> LOCATION: (300)..(301)
<223> OTHER INFORMATION: n=a,c,g or t
<220> FEATURE:
<221> NAME/KEY: unsure
<222> LOCATION: (317)
<223> OTHER INFORMATION: n=a,c,g or t
<220> FEATURE:
<221> NAME/KEY: unsure
<222> LOCATION: (333)
<223> OTHER INFORMATION: n=a,c,g or t
<220> FEATURE:
<221> NAME/KEY: unsure
<222> LOCATION: (336)
<223> OTHER INFORMATION: n=a,c,g or t
<220> FEATURE:
<221> NAME/KEY: unsure
<222> LOCATION: (347)
<223> OTHER INFORMATION: n=a,c,g or t
<220> FEATURE:
<221> NAME/KEY: unsure
<222> LOCATION: (360)
<223> OTHER INFORMATION: n=a,c,g or t
<220> FEATURE:
<221> NAME/KEY: unsure
<222> LOCATION: (367)
```

-continued

```
<223> OTHER INFORMATION: n=a,c,g or t
<220> FEATURE:
<221> NAME/KEY: unsure
<222> LOCATION: (389)
<223> OTHER INFORMATION: n=a,c,g or t
<220> FEATURE:
<221> NAME/KEY: unsure
<222> LOCATION: (406)
<223> OTHER INFORMATION: n=a,c,g or t
<220> FEATURE:
<221> NAME/KEY: unsure
<222> LOCATION: (435)
<223> OTHER INFORMATION: n=a,c,g or t
<220> FEATURE:
<221> NAME/KEY: unsure
<222> LOCATION: (441)
<223> OTHER INFORMATION: n=a,c,g or t

<400> SEQUENCE: 35
cccaccagca gagacgaaga tnccacgagg aaccgttggg atctanctaa ctagctcntc      60
ncgatgatta ccgggaagga catctaccac ntgctggngg nggtggtgcc gctgtacgtg     120
gncatgttca tggcgtacgg gtcggtgcgg tggtggggca tcttcacgcc ggaccantgc    180
tcgggcatca aacgcttcgt ngccgtcttc gcggtggcgc tcctctcctt ccacttcatc    240
tccaccaacg aaccctacgc catggactaa cgcttcctgg gcgccgactc gctgcanaan    300
ntcgttatcc tcgccgncct cgccgtgtgg ganaangtgc ctcccncca acggtgcccn    360 ggggganaga aggcggcgaa ggctcctcnc tgggctggga caacanactc ttctccttgg   420
ggaaagtgcc aaaanactgg ngaagggggaa tccccctgct gggcgcaagt atg          473

<210> SEQ ID NO 36
<211> LENGTH: 89
<212> TYPE: PRT
<213> ORGANISM: Triticum aestivum
<220> FEATURE:
<221> NAME/KEY: UNSURE
<222> LOCATION: (10)
<223> OTHER INFORMATION: Xaa = ANY AMINO ACID
<220> FEATURE:
<221> NAME/KEY: UNSURE
<222> LOCATION: (12)..(13)
<223> OTHER INFORMATION: Xaa = ANY AMINO ACID
<220> FEATURE:
<221> NAME/KEY: UNSURE
<222> LOCATION: (20)
<223> OTHER INFORMATION: Xaa = ANY AMINO ACID
<220> FEATURE:
<221> NAME/KEY: UNSURE
<222> LOCATION: (38)
<223> OTHER INFORMATION: Xaa = ANY AMINO ACID
<220> FEATURE:
<221> NAME/KEY: UNSURE
<222> LOCATION: (69)
<223> OTHER INFORMATION: Xaa = ANY AMINO ACID
<220> FEATURE:
<221> NAME/KEY: UNSURE
<222> LOCATION: (78)..(79)..(80)
<223> OTHER INFORMATION: Xaa = ANY AMINO ACID
<220> FEATURE:
<221> NAME/KEY: UNSURE
<222> LOCATION: (85)
<223> OTHER INFORMATION: Xaa = ANY AMINO ACID

<400> SEQUENCE: 36

Met Ile Thr Gly Lys Asp Ile Tyr His Xaa Leu Xaa Xaa Val Val Pro
  1               5                  10                  15

Leu Tyr Val Xaa Met Phe Met Ala Tyr Gly Ser Val Arg Trp Trp Gly
                 20                  25                  30

Ile Phe Thr Pro Asp Xaa Cys Ser Gly Ile Lys Arg Phe Val Ala Val
             35                  40                  45
```

Phe Ala Val Ala Leu Leu Ser Phe His Phe Ile Ser Thr Asn Glu Pro
        50                  55                  60

Tyr Ala Met Asp Xaa Arg Phe Leu Gly Ala Asp Ser Leu Xaa Xaa Xaa
65                  70                  75                  80

Val Ile Leu Ala Xaa Leu Ala Val Trp
                85

<210> SEQ ID NO 37
<211> LENGTH: 2293
<212> TYPE: DNA
<213> ORGANISM: Triticum aestivum

<400> SEQUENCE: 37

| | | | | | |
|---|---|---|---|---|---|
| ctggatcgat | ccccagcagc | agagacgaga | tcccacgagg | aaccgttggg | atctagctag | 60 |
| ctagctcgtc | gcgatgatca | ccgggaagga | catctacgac | gtgctggcgg | cggtggtgcc | 120 |
| gctgtacgtg | gccatgttca | tggcgtacgg | gtcggtgcgg | tggtggggca | tcttcacgcc | 180 |
| ggaccagtgc | tcgggcatca | accgcttcgt | cgccgtcttc | gcggtgccgc | tcctctcctt | 240 |
| ccacttcatc | tccaccaacg | accctacgc | catggactac | cgcttcctgg | ccgccgactc | 300 |
| gctgcagaag | ctcgtcatcc | tcgccgccct | cgccgtgtgg | cacaacgtgc | tctcccgcta | 360 |
| ccggtgccgc | ggcggcacgg | aggccggcga | ggcctcgtcg | ctggactgga | ccatcacgct | 420 |
| cttctccctg | gcgacgctgc | ccaacacgct | ggtgatgggc | atcccgctgc | tgcgcgccat | 480 |
| gtacggcgac | ttctcggggt | cgctcatggt | gcagatcgtg | gtgctgcaga | gcgtcatctg | 540 |
| gtacacgctc | atgctcttcc | tcttcgagta | ccgcggcgcc | aaggcgctca | tctccgagca | 600 |
| gttcccgccc | gacgtcggcg | ccagcatcgc | ctccttccgc | gtcgactccg | acgtcgtctc | 660 |
| gctcaacggg | cgcgaggcgc | tgcacgccga | cgccgaggtc | ggccgcgacg | gccgcgtcca | 720 |
| cgtcgtcatc | cgccggtccg | cgtcggggtc | caccacgggc | ggccacgcg | ccggcgctc | 780 |
| cgggatctac | cgtggcgcgt | ccaacgccat | gacgccgcgc | gcgtccaacc | tcacgggcgt | 840 |
| ggagatctac | tcgctgcaga | cgtcgcggga | gcccacgccg | aggcagtcca | gcttcaacca | 900 |
| gtccgacttc | tactccatgt | tcaacgggag | caagctggct | agtcccaagg | gccagccccc | 960 |
| cgtcgccgga | ggtggtggtg | cgcgcgggca | ggggctcgac | gagcaggtgg | ccaacaagtt | 1020 |
| caagggcggc | gaggcggctg | cgccctaccc | gcgcccaac | cccgggatga | tgatgccggc | 1080 |
| gccacggaag | aaggagcttg | ggggttccaa | ctcaaactcg | aacaaggagc | tgcacatgtt | 1140 |
| cgtgtggagc | tccagcgcgt | cgcccgtgtc | ggaggccaac | ctccgcaacg | ccgtcaacca | 1200 |
| cgccgcgtcc | accgacttcg | ccgccgcacc | gccggcggca | gccacgccac | gagacggcgc | 1260 |
| cacacccaga | ggcgtgagcg | gcagcgtgac | gccggtgatg | aagaaggacg | ccagcagcgg | 1320 |
| cgcggtggag | gtggagatcg | aggacggcat | gatgaagagc | ccggcgacgg | ggctgggcgc | 1380 |
| caagttcccg | gtgtcggggt | cccctacgt | ggccccgcgg | aagaagggcg | ccgacgtgcc | 1440 |
| tgggctggag | gaggcggcgc | acccgatgcc | gccggcgagc | gtgatgaccc | ggctcatcct | 1500 |
| catcatggtg | tggcgcaagc | tcatccgcaa | ccccaacacc | tactccagcc | tcatcggcct | 1560 |
| cgtctggtca | ctcgtctcct | tcaggtggaa | cattcagatg | cctacaataa | tcaaggggtc | 1620 |
| catatccatc | ctgtctgatg | cagggctagg | atggctatg | ttcagcttag | gtctcttcat | 1680 |
| ggctctgcaa | ccaaagatca | tctcttgcgg | gaagtctgtc | gccacatttg | caatggcagt | 1740 |
| gaggttcttg | actgggccgg | cggtgatcgc | cgcgacctca | atcgccgtcg | ggctccgggg | 1800 |
| agtgctccta | catgttgcca | ttgtccaggc | agcacttcca | caaggaattg | ttccatttgt | 1860 |

```
gttcgccaag gagtacaatt gccatcctca aatacttagc acagcggtta ttttggaat      1920 gctcgtggcg ctcccgatca cgatactcta ctacgttctc cttgggatat agattcataa      1980
tcttgaagaa ccaaggctgc aaatcttcgg gtagggagaa gtagaattct agagagaaaa      2040
tggcaactga acatgcttgt gggctgtcct gaagacctga agatgcatga gaccaagcag      2100
aaggataggg agaactaagt aggaccctag acaggaattc aaaggacaga taaagatatc      2160
cttggttcca ttttttttaat tttttatatt attttttacta ctgttttaga tccaaagtaa      2220
aggctagggc tttgagtatg aagagttcaa ccgttaaatc gaaaaaaaaa aaaaaaaaaa      2280
aaaaaaaaaa aaa                                                          2293

<210> SEQ ID NO 38
<211> LENGTH: 632
<212> TYPE: PRT
<213> ORGANISM: Triticum aestivum

<400> SEQUENCE: 38

Met Ile Thr Gly Lys Asp Ile Tyr Asp Val Leu Ala Ala Val Val Pro
 1               5                  10                  15

Leu Tyr Val Ala Met Phe Met Ala Tyr Gly Ser Val Arg Trp Trp Gly
            20                  25                  30

Ile Phe Thr Pro Asp Gln Cys Ser Gly Ile Asn Arg Phe Val Ala Val
        35                  40                  45

Phe Ala Val Pro Leu Leu Ser Phe His Phe Ile Ser Thr Asn Asp Pro
    50                  55                  60

Tyr Ala Met Asp Tyr Arg Phe Leu Ala Ala Asp Ser Leu Gln Lys Leu
65                  70                  75                  80

Val Ile Leu Ala Ala Leu Ala Val Trp His Asn Val Leu Ser Arg Tyr
                85                  90                  95

Arg Cys Arg Gly Gly Thr Glu Ala Gly Glu Ala Ser Ser Leu Asp Trp
            100                 105                 110

Thr Ile Thr Leu Phe Ser Leu Ala Thr Leu Pro Asn Thr Leu Val Met
        115                 120                 125

Gly Ile Pro Leu Leu Arg Ala Met Tyr Gly Asp Phe Ser Gly Ser Leu
    130                 135                 140

Met Val Gln Ile Val Leu Gln Ser Val Ile Trp Tyr Thr Leu Met Leu
145                 150                 155                 160

Leu Phe Leu Phe Glu Tyr Arg Gly Ala Lys Ala Leu Ile Ser Glu Gln
                165                 170                 175

Phe Pro Pro Asp Val Gly Ala Ser Ile Ala Ser Phe Arg Val Asp Ser
            180                 185                 190

Asp Val Val Ser Leu Asn Gly Arg Glu Ala Leu His Ala Asp Ala Glu
        195                 200                 205

Val Gly Arg Asp Gly Arg Val His Val Ile Arg Arg Ser Ala Ser
    210                 215                 220

Gly Ser Thr Thr Gly Gly His Gly Ala Gly Arg Ser Gly Ile Tyr Arg
225                 230                 235                 240

Gly Ala Ser Asn Ala Met Thr Pro Arg Ala Ser Asn Leu Thr Gly Val
                245                 250                 255

Glu Ile Tyr Ser Leu Gln Thr Ser Arg Glu Pro Thr Pro Arg Gln Ser
            260                 265                 270

Ser Phe Asn Gln Ser Asp Phe Tyr Ser Met Phe Asn Gly Ser Lys Leu
        275                 280                 285

Ala Ser Pro Lys Gly Gln Pro Pro Val Ala Gly Gly Gly Ala Arg
    290                 295                 300
```

```
Gly Gln Gly Leu Asp Glu Gln Val Ala Asn Lys Phe Lys Gly Gly Glu
305                 310                 315                 320

Ala Ala Ala Pro Tyr Pro Ala Pro Asn Pro Gly Met Met Met Pro Ala
                325                 330                 335

Pro Arg Lys Lys Glu Leu Gly Gly Ser Asn Ser Asn Ser Asp Lys Glu
            340                 345                 350

Leu His Met Phe Val Trp Ser Ser Ala Ser Pro Val Ser Glu Ala
        355                 360                 365

Asn Leu Arg Asn Ala Val Asn His Ala Ala Ser Thr Asp Phe Ala Ala
        370                 375                 380

Ala Pro Pro Ala Ala Thr Pro Arg Asp Gly Ala Thr Pro Arg Gly
385                 390                 395                 400

Val Ser Gly Ser Val Thr Pro Val Met Lys Lys Asp Ala Ser Ser Gly
                405                 410                 415

Ala Val Glu Val Glu Ile Glu Asp Gly Met Met Lys Ser Pro Ala Thr
            420                 425                 430

Gly Leu Gly Ala Lys Phe Pro Val Ser Gly Ser Pro Tyr Val Ala Pro
        435                 440                 445

Arg Lys Lys Gly Ala Asp Val Pro Gly Leu Glu Glu Ala Ala His Pro
450                 455                 460

Met Pro Pro Ala Ser Val Met Thr Arg Leu Ile Leu Ile Met Val Trp
465                 470                 475                 480

Arg Lys Leu Ile Arg Asn Pro Asn Thr Tyr Ser Ser Leu Ile Gly Leu
            485                 490                 495

Val Trp Ser Leu Val Ser Phe Arg Trp Asn Ile Gln Met Pro Thr Ile
                500                 505                 510

Ile Lys Gly Ser Ile Ser Ile Leu Ser Asp Ala Gly Leu Gly Met Ala
            515                 520                 525

Met Phe Ser Leu Gly Leu Phe Met Ala Leu Gln Pro Lys Ile Ile Ser
        530                 535                 540

Cys Gly Lys Ser Val Ala Thr Phe Ala Met Ala Val Arg Phe Leu Thr
545                 550                 555                 560

Gly Pro Ala Val Ile Ala Ala Thr Ser Ile Ala Val Gly Leu Arg Gly
                565                 570                 575

Val Leu Leu His Val Ala Ile Val Gln Ala Ala Leu Pro Gln Gly Ile
            580                 585                 590

Val Pro Phe Val Phe Ala Lys Glu Tyr Asn Cys His Pro Gln Ile Leu
        595                 600                 605

Ser Thr Ala Val Ile Phe Gly Met Leu Val Ala Leu Pro Ile Thr Ile
        610                 615                 620

Leu Tyr Tyr Val Leu Leu Gly Ile
625                 630

<210> SEQ ID NO 39
<211> LENGTH: 447
<212> TYPE: DNA
<213> ORGANISM: Triticum aestivum
<220> FEATURE:
<221> NAME/KEY: unsure
<222> LOCATION: (366)
<223> OTHER INFORMATION: n=a,c,g or t
<220> FEATURE:
<221> NAME/KEY: unsure
<222> LOCATION: (380)
<223> OTHER INFORMATION: n=a,c,g or t
<220> FEATURE:
<221> NAME/KEY: unsure
<222> LOCATION: (390)
```

<223> OTHER INFORMATION: n=a,c,g or t
<220> FEATURE:
<221> NAME/KEY: unsure
<222> LOCATION: (418)
<223> OTHER INFORMATION: n=a,c,g or t
<220> FEATURE:
<221> NAME/KEY: unsure
<222> LOCATION: (421)
<223> OTHER INFORMATION: n=a,c,g or t
<220> FEATURE:
<221> NAME/KEY: unsure
<222> LOCATION: (434)
<223> OTHER INFORMATION: n=a,c,g or t

<400> SEQUENCE: 39

```
gcacacagag acagtcatac tactccatca aataagatga tagcgttggg cgacatctac      60
aaggtggtgg aggcgatggc gccgctttac ttcgcgctag gctcgggta cgggtccgtt     120
cgatggtggc ggttcttcac ggcggagcag tgcggcgcca tcaacacgct ggtggtctgc    180
ttctccatgc ccttcttcac cttcgacttc gtggtccgcg ccgacccta cgccatgaat     240
taccgcgtca tcgccgccga cgccgtcgcc aaacttctcg ccgtgctcgc cgcggccgtc    300
tgggcgcgct cgccaaggc caaggccggc gcctactcgt ggtcatcacg gggttctccc    360
tgggcncgta caacaacacn ctcgtcgtcn gggtgccgct tctgggacgc caatttcngg   420
naattggggg gcanggactt tattttt                                        447
```

<210> SEQ ID NO 40
<211> LENGTH: 94
<212> TYPE: PRT
<213> ORGANISM: Triticum aestivum

<400> SEQUENCE: 40

Met Ile Ala Leu Gly Asp Ile Tyr Lys Val Val Glu Ala Met Ala Pro
1               5                   10                  15
Leu Tyr Phe Ala Leu Gly Leu Gly Tyr Gly Ser Val Arg Trp Trp Arg
            20                  25                  30
Phe Phe Thr Ala Glu Gln Cys Gly Ala Ile Asn Thr Leu Val Val Cys
        35                  40                  45
Phe Ser Met Pro Phe Phe Thr Phe Asp Phe Val Val Arg Ala Asp Pro
    50                  55                  60
Tyr Ala Met Asn Tyr Arg Val Ile Ala Ala Asp Ala Val Ala Lys Leu
65                  70                  75                  80
Leu Ala Val Leu Ala Ala Val Trp Ala Arg Cys Ala Lys
            85                  90

<210> SEQ ID NO 41
<211> LENGTH: 415
<212> TYPE: DNA
<213> ORGANISM: Triticum aestivum

<400> SEQUENCE: 41

```
ctcgcctaaa taaacctctc ccccacgcac tccccactc caccacacac cctcaccagc     60
tcgcccgcag agtgagccga ggccgagagc cggagcgcga aggaagaag cagaggaggt    120
cgggcaagat gatcacgggc acggacttct accacgtgat gacggcggtg gtgccgctgt    180
acgtggccat gatcctcgcc tacgcctccg tcaagtggtg gggcatcttc acgccggacc    240
agtgctccgg gatcaaccgc ttcgtcgcgc tcttcgccgt gccgctcctc tccttccact   300
tcatctccac caacaacccc tacaccatga acctgcgctt catcgccgcc gacacgctgc   360
agaagctcat gatgctcgcc atgctcaacg cctggagcaa ctctcccgcc gcggc       415
```

-continued

<210> SEQ ID NO 42
<211> LENGTH: 91
<212> TYPE: PRT
<213> ORGANISM: Triticum aestivum

<400> SEQUENCE: 42

Met Ile Thr Gly Thr Asp Phe Tyr His Val Met Thr Ala Val Val Pro
1               5                   10                  15

Leu Tyr Val Ala Met Ile Leu Ala Tyr Gly Ser Val Lys Trp Trp Gly
                20                  25                  30

Ile Phe Thr Pro Asp Gln Cys Ser Gly Ile Asn Arg Phe Val Ala Leu
            35                  40                  45

Phe Ala Val Pro Leu Leu Ser Phe His Phe Ile Ser Thr Asn Asn Pro
        50                  55                  60

Tyr Thr Met Asn Leu Arg Phe Ile Ala Ala Asp Thr Leu Gln Lys Leu
65                  70                  75                  80

Met Met Leu Ala Met Leu Asn Ala Trp Ser Asn
                85                  90

<210> SEQ ID NO 43
<211> LENGTH: 647
<212> TYPE: PRT
<213> ORGANISM: Arabidopsis thaliana

<400> SEQUENCE: 43

Met Ile Thr Gly Lys Asp Met Tyr Asp Val Leu Ala Ala Met Val Pro
1               5                   10                  15

Leu Tyr Val Ala Met Ile Leu Ala Tyr Gly Ser Val Arg Trp Trp Gly
                20                  25                  30

Ile Phe Thr Pro Asp Gln Cys Ser Gly Ile Asn Arg Phe Val Ala Val
            35                  40                  45

Phe Ala Val Pro Leu Leu Ser Phe His Phe Ile Ser Ser Asn Asp Pro
        50                  55                  60

Tyr Ala Met Asn Tyr His Phe Leu Ala Ala Asp Ser Leu Gln Lys Val
65                  70                  75                  80

Val Ile Leu Ala Ala Leu Phe Leu Trp Gln Ala Phe Ser Arg Arg Gly
                85                  90                  95

Ser Leu Glu Trp Met Ile Thr Leu Phe Ser Leu Ser Thr Leu Pro Asn
                100                 105                 110

Thr Leu Val Met Gly Ile Pro Leu Leu Arg Ala Met Tyr Gly Asp Phe
            115                 120                 125

Ser Gly Asn Leu Met Val Gln Ile Val Val Leu Gln Ser Ile Ile Trp
        130                 135                 140

Tyr Thr Leu Met Leu Phe Leu Phe Glu Phe Arg Gly Ala Lys Leu Leu
145                 150                 155                 160

Ile Ser Glu Gln Phe Pro Glu Thr Ala Gly Ser Ile Thr Ser Phe Arg
                165                 170                 175

Val Asp Ser Asp Val Ile Ser Leu Asn Gly Arg Glu Pro Leu Gln Thr
            180                 185                 190

Asp Ala Glu Ile Gly Asp Asp Gly Lys Leu His Val Val Arg Arg
        195                 200                 205

Ser Ser Ala Ala Ser Ser Met Ile Ser Ser Phe Asn Lys Ser His Gly
    210                 215                 220

Gly Gly Leu Asn Ser Ser Met Ile Thr Pro Arg Ala Ser Asn Leu Thr
225                 230                 235                 240

Gly Val Glu Ile Tyr Ser Val Gln Ser Ser Arg Glu Pro Thr Pro Arg

```
                         245                 250                 255
Ala Ser Ser Phe Asn Gln Thr Asp Phe Tyr Ala Met Phe Asn Ala Ser
                260                 265                 270

Lys Ala Pro Ser Pro Arg His Gly Tyr Thr Asn Ser Tyr Gly Gly Ala
            275                 280                 285

Gly Ala Gly Pro Gly Gly Asp Val Tyr Ser Leu Gln Ser Ser Lys Gly
        290                 295                 300

Val Thr Pro Arg Thr Ser Asn Phe Asp Glu Val Met Lys Thr Ala
305                 310                 315                 320

Lys Lys Ala Gly Arg Gly Gly Arg Ser Met Ser Gly Glu Leu Tyr Asn
                325                 330                 335

Asn Asn Ser Val Pro Ser Tyr Pro Pro Asn Pro Met Phe Thr Gly
            340                 345                 350

Ser Thr Ser Gly Ala Ser Gly Val Lys Lys Glu Ser Gly Gly
        355                 360                 365

Gly Ser Gly Gly Val Gly Val Gly Gly Gln Asn Lys Glu Met Asn
        370                 375                 380

Met Phe Val Trp Ser Ser Ala Ser Pro Val Ser Glu Ala Asn Ala
385                 390                 395                 400

Lys Asn Ala Met Thr Arg Gly Ser Ser Thr Asp Val Ser Thr Asp Pro
                405                 410                 415

Lys Val Ser Ile Pro Pro His Asp Asn Leu Ala Thr Lys Ala Met Gln
            420                 425                 430

Asn Leu Ile Glu Asn Met Ser Pro Gly Arg Lys Gly His Val Glu Met
            435                 440                 445

Asp Gln Asp Gly Asn Asn Gly Gly Lys Ser Pro Tyr Met Gly Lys Lys
        450                 455                 460

Gly Ser Asp Val Glu Asp Gly Gly Pro Gly Pro Arg Lys Gln Gln Met
465                 470                 475                 480

Pro Pro Ala Ser Val Met Thr Arg Leu Ile Leu Ile Met Val Trp Arg
                485                 490                 495

Lys Leu Ile Arg Asn Pro Asn Thr Tyr Ser Ser Leu Phe Gly Leu Ala
            500                 505                 510

Trp Ser Leu Val Ser Phe Lys Trp Asn Ile Lys Met Pro Thr Ile Met
        515                 520                 525

Ser Gly Ser Ile Ser Ile Leu Ser Asp Ala Gly Leu Gly Met Ala Met
        530                 535                 540

Phe Ser Leu Gly Leu Phe Met Ala Leu Gln Pro Lys Ile Ile Ala Cys
545                 550                 555                 560

Gly Lys Ser Val Ala Gly Phe Ala Met Ala Val Arg Phe Leu Thr Gly
                565                 570                 575

Pro Ala Val Ile Ala Ala Thr Ser Ile Ala Ile Gly Ile Arg Gly Asp
            580                 585                 590

Leu Leu His Ile Ala Ile Val Gln Ala Ala Leu Pro Gln Gly Ile Val
            595                 600                 605

Pro Phe Val Phe Ala Lys Glu Tyr Asn Val His Pro Asp Ile Leu Ser
        610                 615                 620

Thr Ala Val Ile Phe Gly Met Leu Val Ala Leu Pro Val Thr Val Leu
625                 630                 635                 640

Tyr Tyr Val Leu Leu Gly Leu
                645

<210> SEQ ID NO 44
<211> LENGTH: 622
```

```
<212> TYPE: PRT
<213> ORGANISM: Arabidopsis thaliana

<400> SEQUENCE: 44

Met Ile Thr Ala Ala Asp Phe Tyr His Val Met Thr Ala Met Val Pro
 1               5                  10                  15

Leu Tyr Val Ala Met Ile Leu Ala Tyr Gly Ser Val Lys Trp Trp Lys
            20                  25                  30

Ile Phe Thr Pro Asp Gln Cys Ser Gly Ile Asn Arg Phe Val Ala Leu
        35                  40                  45

Phe Ala Val Pro Leu Leu Ser Phe His Phe Ile Ala Ala Asn Asn Pro
    50                  55                  60

Tyr Ala Met Asn Leu Arg Phe Leu Ala Ala Asp Ser Leu Gln Lys Val
 65                  70                  75                  80

Ile Val Leu Ser Leu Leu Phe Leu Trp Cys Lys Leu Ser Arg Asn Gly
                85                  90                  95

Ser Leu Asp Trp Thr Ile Thr Leu Phe Ser Leu Ser Thr Leu Pro Asn
            100                 105                 110

Thr Leu Val Met Gly Ile Pro Leu Leu Lys Gly Met Tyr Gly Asn Phe
        115                 120                 125

Ser Gly Asp Leu Met Val Gln Ile Val Val Leu Gln Cys Ile Ile Trp
    130                 135                 140

Tyr Ile Leu Met Leu Phe Leu Phe Glu Tyr Arg Gly Ala Lys Leu Leu
145                 150                 155                 160

Ile Ser Glu Gln Phe Pro Asp Thr Ala Gly Ser Ile Val Ser Ile His
                165                 170                 175

Val Asp Ser Asp Ile Met Ser Leu Asp Gly Arg Gln Pro Leu Glu Thr
            180                 185                 190

Glu Ala Glu Ile Lys Glu Asp Gly Lys Leu His Val Thr Val Arg Arg
        195                 200                 205

Ser Asn Ala Ser Arg Ser Asp Ile Tyr Ser Arg Ser Gln Gly Leu
    210                 215                 220

Ser Ala Thr Pro Arg Pro Ser Asn Leu Thr Asn Ala Glu Ile Tyr Ser
225                 230                 235                 240

Leu Gln Ser Ser Arg Asn Pro Thr Pro Arg Gly Ser Ser Phe Asn His
                245                 250                 255

Thr Asp Phe Tyr Ser Met Met Ala Ser Gly Gly Arg Asn Ser Asn
            260                 265                 270

Phe Gly Pro Gly Glu Ala Val Phe Gly Ser Lys Gly Pro Thr Pro Arg
        275                 280                 285

Pro Ser Asn Tyr Glu Glu Asp Gly Gly Pro Ala Lys Pro Thr Ala Ala
    290                 295                 300

Gly Thr Ala Ala Gly Ala Gly Arg Phe His Tyr Gln Ser Gly Gly Ser
305                 310                 315                 320

Gly Gly Gly Gly Gly Ala His Tyr Pro Ala Pro Asn Pro Gly Met Phe
                325                 330                 335

Ser Pro Asn Thr Gly Gly Gly Gly Thr Ala Ala Lys Gly Asn Ala
            340                 345                 350

Pro Val Val Gly Gly Lys Arg Gln Asp Gly Asn Gly Arg Asp Leu His
        355                 360                 365

Met Phe Val Trp Ser Ser Ser Ala Ser Pro Val Ser Asp Val Phe Gly
    370                 375                 380

Gly Gly Gly Gly Asn His His Ala Asp Tyr Ser Thr Ala Thr Asn Asp
385                 390                 395                 400
```

```
His Gln Lys Asp Val Lys Ile Ser Val Pro Gln Gly Asn Ser Asn Asp
                405                 410                 415
Asn Gln Tyr Val Glu Arg Glu Glu Phe Ser Phe Gly Asn Lys Asp Asp
            420                 425                 430
Asp Ser Lys Val Leu Ala Thr Asp Gly Gly Asn Asn Ile Ser Asn Lys
        435                 440                 445
Thr Thr Gln Ala Lys Val Met Pro Pro Thr Ser Val Met Thr Arg Leu
    450                 455                 460
Ile Leu Ile Met Val Trp Arg Lys Leu Ile Arg Asn Pro Asn Ser Tyr
465                 470                 475                 480
Ser Ser Leu Phe Gly Ile Thr Trp Ser Leu Ile Ser Phe Lys Trp Asn
                485                 490                 495
Ile Glu Met Pro Ala Leu Ile Ala Lys Ser Ile Ser Ile Leu Ser Asp
            500                 505                 510
Ala Gly Leu Gly Met Ala Met Phe Ser Leu Gly Leu Phe Met Ala Leu
        515                 520                 525
Asn Pro Arg Ile Ile Ala Cys Gly Asn Arg Arg Ala Ala Phe Ala Ala
    530                 535                 540
Ala Met Arg Phe Val Val Gly Pro Ala Val Met Leu Val Ala Ser Tyr
545                 550                 555                 560
Ala Val Gly Leu Arg Gly Val Leu Leu His Val Ala Ile Ile Gln Ala
                565                 570                 575
Ala Leu Pro Gln Gly Ile Val Pro Phe Val Phe Ala Lys Glu Tyr Asn
            580                 585                 590
Val His Pro Asp Ile Leu Ser Thr Ala Val Ile Phe Gly Met Leu Ile
        595                 600                 605
Ala Leu Pro Ile Thr Leu Leu Tyr Tyr Ile Leu Leu Gly Leu
    610                 615                 620

<210> SEQ ID NO 45
<211> LENGTH: 425
<212> TYPE: DNA
<213> ORGANISM: Triticum aestivum

<400> SEQUENCE: 45
gcacgagctc gcctaaataa acctctcccc cacgcactcc cccactccac cacacaccct    60
caccagctcg cccgcagagt gagccgaggc cgagagccgg agcgcgagag gaagaagcag   120
aggaggtcgg gcaagatgat cacgggcacg gacttctacc acgtgatgac ggcggtggtg   180
ccgctgtacg tggccatgat cctcgcctac ggctccgtca agtggtgggg catcttcacg   240
ccggaccagt gctccgggat caaccgcttc gtcgcgctct cgccgtgcc gctcctctcc    300
ttccacttca tctccaccaa caaccccta c accatgaacc tgcgcttcat cgccgccgac   360
acgctgcaga agctcatgat gctcgccatg ctcaccgcct ggagccacct ctcccgccgc   420
ggcag                                                              425

<210> SEQ ID NO 46
<211> LENGTH: 96
<212> TYPE: PRT
<213> ORGANISM: Triticum aestivum

<400> SEQUENCE: 46

Met Ile Thr Gly Thr Asp Phe Tyr His Val Met Thr Ala Val Val Pro
  1               5                  10                  15
Leu Tyr Val Ala Met Ile Leu Ala Tyr Gly Ser Val Lys Trp Trp Gly
             20                  25                  30
```

Ile Phe Thr Pro Asp Gln Cys Ser Gly Ile Asn Arg Phe Val Ala Leu
          35                  40                  45

Phe Ala Val Pro Leu Leu Ser Phe His Phe Ile Ser Thr Asn Asn Pro
 50                  55                  60

Tyr Thr Met Asn Leu Arg Phe Ile Ala Ala Asp Thr Leu Gln Lys Leu
 65                  70                  75                  80

Met Met Leu Ala Met Leu Thr Ala Trp Ser His Leu Ser Arg Arg Gly
             85                  90                  95

<210> SEQ ID NO 47
<211> LENGTH: 855
<212> TYPE: DNA
<213> ORGANISM: Zea mays

<400> SEQUENCE: 47

```
ccacgcgtcc ggctgatcgt cctggcgctg ctcactgcat ggagctacct ctcccgccgg      60
ggctgcctcg agtggaccat cacgctcttc tccctgtcga cgctgcccaa cacgctggtg     120
atgggcatcc cgctgctcaa gggcatgtac ggcgacttct ccggcagcct catggtgcag     180
atcgtggtgc tccagtgcat catctggtac acgctgatgc tgttcatgtt cgagtaccgc     240
ggcgccagga tcctcatcac cgagcagttc cccgacacgc cggcgccat cgcctccatc      300
gtggtggacc ccgacgtggt gtcgctggac gggcgcaacg acgccatcga cgcgaggcc      360
gaggtgaagg aggacggcaa gatacacgtc accgtgcggc gctccaacgc gtcgcgctcg     420
gacatctact cccggcggtc catggggttc tccagcacca cgccgcggcc cagcaacctg     480
accaacgccg agatctactc gctgcagtcg tcgaggaacc ccacgccgcg gggctccagc     540
ttcaaccaca ccgacttcta ctccatggtc ggccgcagct ccaacttcgc cgccggggac     600
gcgttcggcc tgcgcacggg cgccacgccc aggccgtcca actacgagga ggacccgcag     660
ggcaaggcga acaagtacgg ccagtacccg cgcgcccaac cggccatggc ggcgcagccc     720
gccaagggcc tcaagaaggc ggccaatggg caggccaagg cgaggacgg caaggaccta     780
cacatgttcg tgtggagctc cagcgcgtcg cccgtgtccg acgtgttcgg caatggcgcc     840
gccgagtaca acgac                                                     855
```

<210> SEQ ID NO 48
<211> LENGTH: 285
<212> TYPE: PRT
<213> ORGANISM: Zea mays

<400> SEQUENCE: 48

Pro Arg Val Arg Leu Ile Val Leu Ala Leu Leu Thr Ala Trp Ser Tyr
 1               5                  10                  15

Leu Ser Arg Arg Gly Cys Leu Glu Trp Thr Ile Thr Leu Phe Ser Leu
             20                  25                  30

Ser Thr Leu Pro Asn Thr Leu Val Met Gly Ile Pro Leu Leu Lys Gly
         35                  40                  45

Met Tyr Gly Asp Phe Ser Gly Ser Leu Met Val Gln Ile Val Val Leu
 50                  55                  60

Gln Cys Ile Ile Trp Tyr Thr Leu Met Leu Phe Met Phe Glu Tyr Arg
 65                  70                  75                  80

Gly Ala Arg Ile Leu Ile Thr Glu Gln Phe Pro Asp Thr Ala Gly Ala
             85                  90                  95

Ile Ala Ser Ile Val Val Asp Pro Asp Val Val Ser Leu Asp Gly Arg
         100                 105                 110

Asn Asp Ala Ile Glu Thr Glu Ala Glu Val Lys Glu Asp Gly Lys Ile

-continued

```
            115                 120                 125
His Val Thr Val Arg Arg Ser Asn Ala Ser Arg Ser Asp Ile Tyr Ser
    130                 135                 140

Arg Arg Ser Met Gly Phe Ser Ser Thr Thr Pro Arg Pro Ser Asn Leu
145                 150                 155                 160

Thr Asn Ala Glu Ile Tyr Ser Leu Gln Ser Ser Arg Asn Pro Thr Pro
                165                 170                 175

Arg Gly Ser Ser Phe Asn His Thr Asp Phe Tyr Ser Met Val Gly Arg
            180                 185                 190

Ser Ser Asn Phe Ala Ala Gly Asp Ala Phe Gly Leu Arg Thr Gly Ala
            195                 200                 205

Thr Pro Arg Pro Ser Asn Tyr Glu Glu Asp Pro Gln Gly Lys Ala Asn
    210                 215                 220

Lys Tyr Gly Gln Tyr Pro Ala Pro Asn Pro Ala Met Ala Ala Gln Pro
225                 230                 235                 240

Ala Lys Gly Leu Lys Lys Ala Ala Asn Gly Gln Ala Lys Gly Glu Asp
                245                 250                 255

Gly Lys Asp Leu His Met Phe Val Trp Ser Ser Ser Ala Ser Pro Val
            260                 265                 270

Ser Asp Val Phe Gly Asn Gly Ala Ala Glu Tyr Asn Asp
    275                 280                 285
```

AUXIN TRANSPORT PROTEINS

This application is a divisional of U.S. patent application Ser. No. 12/173,868 filed Jul. 16, 200, now U.S. Pat. No. 7,638,681, issued Dec. 29, 2009, which is a divisional of U.S. patent application Ser. No. 10/987,855, filed Nov. 12, 2004, now U.S. Pat. No. 7,422,901, issued Sept. 9, 2008, which is a continuation of U.S. patent application Ser. No. 10/030,884, filed Oct. 25, 2001, now abandoned, which is a 35 U.S.C. 371 National Stage Application of International Application No. PCT/US00/12061, filed May 3, 2000, which claims the priority from U.S. Provisional Application No. 60/133,040, filed May 7, 1999. The entire contents of each of these applications is incorporated herein by reference.

FIELD OF THE INVENTION

This invention is in the field of plant molecular biology. More specifically, this invention pertains to nucleic acid fragments encoding auxin transport proteins in plants and seeds.

BACKGROUND OF THE INVENTION

Auxins are a major class of plant hormones that influence diverse aspects of plant behavior and development including vascular tissue differentiation, apical development, tropic responses, and organ (e.g., flower, leaf) development. The term "auxin" refers to a diverse group of natural and synthetic chemical substances that are able to stimulate elongation growth in coleoptiles and many stems. Indole-3-acetic acid (IAA) is the principal auxin in higher plants, though other molecules such as 4-chloroindole-3-acetic acid and phenylacetic acid have been shown to have auxin activity. Synthetic auxins include 2,4,5-trichlorophenoxyacetic acid (2,4,5-T) and 2,4-dichlorophenoxyacetic acid (2,4-D); both are commonly used as herbicides.

Distribution of auxins in concentration gradients within plant organs enables auxins to convey to cells their relative location, allowing the plants to respond accordingly to a given stimulus. A classic example that illustrates auxin action is the differential growth and curvature of etiolated coleoptiles exposed to light. It is believed that the phototropic stimulus results in a lateral redistribution of auxin in the coleoptile such that the shaded side has a higher auxin concentration than the illuminated side. With more auxin stimulating cell elongation on the shaded side, the end-result is the apparent bending of the coleoptile towards the light source.

The foregoing description underscores the importance of polar transport in auxin function. Not surprisingly, a number of genetic and physiological studies have focused on the polar auxin transport system operating in plant cells. *Arabidopsis* mutants with impaired auxin transport capabilities exhibit varying phenotypes: pin1 mutants develop naked, pin-like inflorescence with few normal flowers (Gälweiler, L. et al., (1998) *Science* 282:2226-2230), while defects in pint (also called eir1 and agr1) are restricted to the root, altering growth and gravitropic response (Luschnig, C. et al., (1998) *Genes Dev.* 12:2175-2187). Proteins encoded by AUX1, PIN1 and PIN2 genes which have been identified to be important for auxin transport and are putative membrane proteins that have significant homology with a number of bacterial membrane transporters (Luschnig, C. et al. supra; Gälweiler L. et al., (1998) *Science* 282:2226-2230; Bennett, M. J. et al., (1996) *Science* 273:948-950; WO 99/63092-A1; U.S. Application No. 60/087,789; EP 0 814 161 A1), consistent with a role for these proteins in auxin transport.

Since auxin affects several aspects of plant development, and polar transport is a vital component of auxin function, it is envisioned that proteins involved in auxin polar transport may serve as potential targets for new herbicide discovery and design. Blocking of normal function of these auxin transport proteins can cause severe plant growth defects; this is supported by the phenotype of mutants where a particular auxin transport protein has been rendered nonfunctional, particularly the *Arabidopsis* pin1 mutants. In addition, since some of these auxin transport proteins have been shown to be root-specific and impact root development to a significant degree, manipulation of auxin transport proteins may be a powerful strategy for developing more robust root systems in plants, which in turn may enhance food production, especially in arid climates.

SUMMARY OF THE INVENTION

The present invention concerns an isolated polynucleotide comprising a nucleotide sequence selected from the group consisting of: (a) a first nucleotide sequence encoding a polypeptide of at least 30 amino acids having at least 85% identity based on the Clustal method of alignment when compared to a polypeptide of SEQ ID NO:6; (b) a second nucleotide sequence encoding a polypeptide of at least 50 amino acids having at least 80% identity based on the Clustal method of alignment when compared to a polypeptide selected from the group consisting of SEQ ID NOs:16, 28, 36, and 40; (c) a third nucleotide sequence encoding a polypeptide of at least 50 amino acids having at least 85% identity based on the Clustal method of alignment when compared to a polypeptide of SEQ ID NO:12; (d) a fourth nucleotide sequence encoding a polypeptide of at least 50 amino acids having at least 90% identity based on the Clustal method of alignment when compared to a polypeptide selected from the group consisting of SEQ ID NOs:8 and 24; (e) a fifth nucleotide sequence encoding a polypeptide of at least 50 amino acids having at least 95% identity based on the Clustal method of alignment when compared to a polypeptide selected from the group consisting of SEQ ID NOs:18 and 32; (f) a sixth nucleotide sequence encoding a polypeptide of at least 90 amino acids having at least 95% identity based on the Clustal method of alignment when compared to a polypeptide of SEQ ID NO:42; (g) a seventh nucleotide sequence encoding a polypeptide of at least 95 amino acids that has at least 95% identity based on the Clustal method of alignment when compared to a polypeptide of SEQ ID NO:46; (h) an eighth nucleotide sequence encoding a polypeptide of at least 100 amino acids having at least 80% identity based on the Clustal method of alignment when compared to a polypeptide selected from the group consisting of SEQ ID NO:20; (i) a ninth nucleotide sequence encoding a polypeptide of at least 100 amino acids having at least 90% identity based on the Clustal method of alignment when compared to a polypeptide of SEQ ID NO:2; (j) a tenth nucleotide sequence encoding a polypeptide of at least 150 amino acids having at least 95% identity based on the Clustal method of alignment when compared to a polypeptide of SEQ ID NO:4; (k) an eleventh nucleotide sequence encoding a polypeptide of at least 300 amino acids having at least 80% identity based on the Clustal method of alignment when compared to a polypeptide of SEQ ID NO:38; (l) a twelfth nucleotide sequence encoding a polypeptide of at least 350 amino acids having at least 95% identity based on the Clustal method of alignment when compared to a polypeptide of SEQ ID NO:10; (m) a thirteenth nucleotide sequence encoding a polypeptide of at least 400 amino acids having at least 80% identity based on the Clustal method of alignment when compared to a polypeptide selected from the group consisting of SEQ ID NOs:22, 26 and 30; (n) a fourteenth nucleotide sequence encoding a polypeptide of at least 500 amino acids having at least 80% identity based on the Clustal method of alignment when compared to a polypeptide of SEQ ID NO:34; (o) a fifteenth nucleotide sequence encoding a polypeptide of at least 200 amino acids having at least 80% identity based on the Clustal method of alignment when compared to a polypeptide of SEQ ID NO:14; (p) a sixteenth nucleotide sequence encoding a polypeptide of at least 250 amino acids having at least 90% identity based on the Clustal method of alignment when compared to a polypeptide of SEQ ID NO:48; and (q) a seventeenth nucleotide sequence comprising the complement of (a), (b), (c), (d), (e), (f), (g), (h), (i), (j), (k), (l), (m), (n), (o), or (p).

In a second embodiment, it is preferred that the isolated polynucleotide of the claimed invention comprises a first nucleotide sequence which comprises a nucleic acid sequence selected from the group consisting of SEQ ID NOs: 1, 3, 5, 7, 9, 11, 13, 15, 17, 19, 21, 23, 25, 27, 29, 31, 33, 35, 37, 39, 41, 45, and 47 that codes for the polypeptide selected from the group consisting of SEQ ID NOs:2, 4, 6, 8, 10, 12, 14, 16, 18, 20, 22, 24, 26, 28, 30, 32, 34, 36, 38, 40, 42, 46, and 48.

In a third embodiment, this invention concerns an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 45, and 47 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns a host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing a host cell comprising a chimeric gene of the present invention or an isolated polynucleotide of the present invention, the process comprising either transforming or transfecting a compatible host cell with a chimeric gene or isolated polynucleotide of the present invention.

In a seventh embodiment, the invention concerns an auxin transport polypeptide selected from the group consisting of: (a) a polypeptide of at least 30 amino acids having at least 85% identity based on the Clustal method of alignment when compared to a polypeptide of SEQ ID NO:6; (b) a polypeptide of at least 50 amino acids having at least 80% identity based on the Clustal method of alignment when compared to a polypeptide selected from the group consisting of SEQ ID NOs:16, 28, 36, and 40; (c) a polypeptide of at least 50 amino acids having at least 85% identity based on the Clustal method of alignment when compared to a polypeptide of SEQ ID NO:12; (d) a polypeptide of at least 50 amino acids having at least 90% identity based on the Clustal method of alignment when compared to a polypeptide selected from the group consisting of SEQ ID NOs:8 and 24; (e) a polypeptide of at least 50 amino acids having at least 95% identity based on the Clustal method of alignment when compared to a polypeptide selected from the group consisting of SEQ ID NOs:18 and 32; (f) a polypeptide of at least 90 amino acids having at least 95% identity based on the Clustal method of alignment when compared to a polypeptide of SEQ ID NO:42; (g) a polypeptide of at least 95 amino acids having at least 95% identity based on the Clustal method of alignment when compared to a polypeptide of SEQ ID NO:46; (h) a polypeptide of at least 100 amino acids having at least 80% identity based on the Clustal method of alignment when compared to a polypeptide selected from the group consisting of SEQ ID NO:20; (i) a polypeptide of at least 100 amino acids having at least 90% identity based on the Clustal method of alignment when compared to a polypeptide of SEQ ID NO:2; (j) a polypeptide of at least 150 amino acids having at least 95% identity based on the Clustal method of alignment when compared to a polypeptide of SEQ ID NO:4; (k) a polypeptide of at least 300 amino acids having at least 80% identity based on the Clustal method of alignment when compared to a polypeptide of SEQ ID NO:38; (l) a polypeptide of at least 350 amino acids having at least 95% identity based on the Clustal method of alignment when compared to a polypeptide of SEQ ID NO:10; (m) a polypeptide of at least 400 amino acids having at least 80% identity based on the Clustal method of alignment when compared to a polypeptide selected from the group consisting of SEQ ID NOs:22, 26 and 30; (n) a polypeptide of at least 500 amino acids having at least 80% identity based on the Clustal method of alignment when compared to a polypeptide of SEQ ID NO:34; (o) a polypeptide of at least 200 amino acids having at least 80% identity based on the Clustal method of alignment when compared to a polypeptide of SEQ ID NO:14; and (p) a polypeptide of at least 250 amino acids having at least 90% identity based on the Clustal method of alignment when compared to a polypeptide of SEQ ID NO:48.

In an eighth embodiment, the invention relates to a method of selecting an isolated polynucleotide that affects the level of expression of an auxin transport polypeptide or enzyme activity in a host cell, preferably a plant cell, the method comprising the steps of: (a) constructing an isolated polynucleotide of the present invention or a chimeric gene of the present invention; (b) introducing the isolated polynucleotide or the chimeric gene into a host cell; (c) measuring the level of the auxin transport polypeptide or enzyme activity in the host cell containing the isolated polynucleotide; and (d) comparing the level of the auxin transport polypeptide or enzyme activity in the host cell containing the isolated polynucleotide with the level of the auxin transport polypeptide or enzyme activity in the host cell that does not contain the isolated polynucleotide.

In a ninth embodiment, the invention concerns a method of obtaining a nucleic acid fragment encoding a substantial portion of an auxin transport polypeptide, preferably a plant auxin transport polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 45, and 47 and the complement of such nucleotide sequences; and amplifying a nucleic acid fragment (preferably a cDNA inserted in a cloning vector) using the oligonucleotide primer. The amplified nucleic acid fragment preferably will encode a substantial portion of an auxin transport polypeptide amino acid sequence.

In a tenth embodiment, this invention relates to a method of obtaining a nucleic acid fragment encoding all or a substantial portion of the amino acid sequence encoding an auxin transport polypeptide comprising the steps of probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide or isolated polypeptide of the present invention.

In a twelfth embodiment, this invention concerns a method for positive selection of a transformed cell comprising: (a) transforming a host cell with the chimeric gene of the present invention or a construct of the present invention; and (b) growing the transformed host cell, preferably a plant cell, such as a monocot or a dicot, under conditions which allow expression of the auxin transport polypeptide polynucleotide in an amount sufficient to complement a null mutant to provide a positive selection means.

A further embodiment of the instant invention is a method for evaluating at least one compound for its ability to inhibit the activity of an auxin transport protein, the method comprising the steps of: (a) transforming a host cell with a chimeric gene comprising a nucleic acid fragment encoding an auxin transport polypeptide, operably linked to at least one suitable regulatory sequence, (b) growing the transformed host cell under conditions that are suitable for expression of the chimeric gene wherein expression of the chimeric gene results in production of the encoded auxin transport protein in the transformed host cell; (c) optionally purifying the auxin transport polypeptide expressed by the transformed host cell; (d) treating the auxin transport polypeptide with a compound to be tested; and (e) comparing the activity of the auxin transport polypeptide that has been treated with a test compound to the activity of an untreated auxin transport polypeptide, thereby selecting compounds with potential for inhibitory activity.

In a further embodiment, the instant invention concerns a method of modulating expression of an auxin transport protein in a plant, comprising the steps of: (a) transforming a plant cell with a nucleic acid fragment encoding the auxin transport protein operably linked in sense or antisense orientation to a promoter; and (b) growing the plant cell under plant growing conditions to produce a regenerated plant capable of expressing the nucleic acid for a time sufficient to modulate expression of the nucleic acid fragment in the plant compared to a corresponding non-transformed plant, thereby resulting in at least one of the following: a more robust root system, an altered root angle, or redirected root growth.

BRIEF DESCRIPTION OF THE DRAWING AND SEQUENCE LISTINGS

The invention can be more fully understood from the following detailed description, the accompanying drawing and Sequence Listing which form a part of this application.

FIG. 1 depicts the amino acid sequence alignment between the auxin transport protein encoded by the nucleotide sequences derived from the corn clone p0119. cmtn124r (SEQ ID NO:14), soybean clone sfl1. pk131. g 9 (SEQ ID NO:30), soybean clone src3c.pk026. o 11 (SEQ ID NO:34), and wheat clone wdk1c.pk008. g 12 (SEQ ID NO:38), the auxin transport protein EIR1 from *Arabidopsis thaliana* (NCBI GenBank Identifier (GI) No. 3377507; SEQ ID NO:43), and the auxin transport protein AtPIN1 from *Arabidopsis thaliana* (NCBI GenBank Identifier (GI) No. 4151319; SEQ ID NO:44). Amino acids which are conserved among all and at least two sequences with an amino acid at that position are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), sequences of the entire cDNA inserts comprising the indicated cDNA clones ("FIS"), contigs assembled from two or more ESTs ("Contig"), contigs assembled from an FIS and one or more ESTs ("Contig*"), or sequences encoding at a minimum the mature protein derived from an EST, FIS, a contig, or an FIS and PCR ("CGS"). Nucleotide SEQ ID NOs:5, 7, 11, 17, 23, 27, 31, 35, and 41 correspond to nucleotide SEQ ID NOs:1, 3, 5, 7, 9, 11, 13, 15, and 17, respectively, presented in U.S. Provisional Application No. 60/133,040, filed May 7, 1999. Amino acid SEQ ID NOs:6, 8, 12, 18, 24, 28, 32, 36, and 42 correspond to amino acid SEQ ID NOs:2, 4, 6, 8, 10, 12, 14, 16, and 18, respectively, presented in U.S. Provisional Application No. 60/133,040, filed May 7, 1999. The sequence descriptions and Sequence Listing attached hereto comply with the rules governing nucleotide and/or amino acid sequence disclosures in patent applications as set forth in 37 C.F.R. §1.821-1.825.

TABLE 1

Auxin Transport Proteins

| | | | SEQ ID NO: | |
| Protein (Plant Source) | Clone Designation | Status | (Nucleotide) | (Amino Acid) |
| --- | --- | --- | --- | --- |
| Auxin Transport Protein (Corn) | ceb1.pk0082.a5 | EST | 1 | 2 |
| Auxin Transport Protein (Corn) | Contig of:<br>cr1.pk0022.a4<br>cr1n.pk0033.e3<br>csi1n.pk0045.a5<br>csi1n.pk0050.d5<br>p0005.cbmej72r<br>p0041.crtba02r | Contig | 3 | 4 |
| Auxin Transport Protein (Corn) | p0016.ctsag12r | EST | 5 | 6 |
| Auxin Transport Protein (Corn) | Contig of:<br>p0097.cqrai63r<br>p0094.csssh17r | Contig | 7 | 8 |

TABLE 1-continued

Auxin Transport Proteins

| Protein (Plant Source) | Clone Designation | Status | SEQ ID NO: (Nucleotide) | SEQ ID NO: (Amino Acid) |
|---|---|---|---|---|
| Auxin Transport Protein (Corn) | p0094.csssh.17r | FIS | 9 | 10 |
| Auxin Transport Protein (Corn) | p0119.cmtnl24r | EST | 11 | 12 |
| Auxin Transport Protein (Corn) | cil1c.pk001.b7 | FIS | 47 | 48 |
| Auxin Transport Protein (Corn) | p0119.cmtnl24r | CGS | 13 | 14 |
| Auxin Transport Protein (Rice) | rr1.pk0019.c4 | EST | 15 | 16 |
| Auxin Transport Protein (Rice) | rsl1n.pk003.n3 | EST | 17 | 18 |
| Auxin Transport Protein (Rice) | rsl1n.pk003.n3 | FIS | 19 | 20 |
| Auxin Transport Protein (Soybean) | scr1c.pk003.g7 | FIS | 21 | 22 |
| Auxin Transport Protein (Soybean) | sdp4c.pk003.h2 | EST | 23 | 24 |
| Auxin Transport Protein (Soybean) | sdp4c.pk003.h2 | FIS | 25 | 26 |
| Auxin Transport Protein (Soybean) | sfl1.pk131.g9 | EST | 27 | 28 |
| Auxin Transport Protein (Soybean) | sfl1.pk131.g9(FIS) | CGS | 29 | 30 |
| Auxin Transport Protein (Soybean) | src3c.pk026.o11 | EST | 31 | 32 |
| Auxin Transport Protein (Soybean) | src3c.pk026.o11(FIS) | CGS | 33 | 34 |
| Auxin Transport Protein (Wheat) | wdk1c.pk008.g12 | EST | 35 | 36 |
| Auxin Transport Protein (Wheat) | wdk1c.pk008.g12(FIS) | CGS | 37 | 38 |
| Auxin Transport Protein (Wheat) | wdr1f.pk001.g9 | EST | 39 | 40 |
| Auxin Transport Protein (Wheat) | wle1n.pk0109.h1 | EST | 41 | 42 |
| Auxin Transport Protein (Wheat) | wle1n.pk0109.h1 | FIS | 45 | 46 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the Biochemical J. 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, 15, 17, 19, 21, 23, 25, 27, 29, 31, 33, 35, 37, 39, 41, 45, 47 or the complement of such sequences.

The term "isolated polynucleotide" refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, 11, 13, 15, 17, 19, 21, 23, 25, 27, 29, 31, 33, 35, 37, 39, 41, 45, and 47 and the complement of such nucleotide sequences may be used in methods of selecting an isolated polynucleotide that affects the expression of an auxin transport polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or a chimeric gene of the present invention; introducing the isolated polynucleotide or the chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 30 or 50 amino acids, preferably at least 90 or 100 amino acids, more preferably at least 150 amino acids, still more preferably at least 200 amino acids, and most preferably at least 250, 300, 350, 400 or 500 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan) appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3' Non-coding sequences" refers to nucleotide sequences located downstream of a coding sequence and includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense RNA" refers to an RNA transcript that includes the mRNA and can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. "Expression" may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. In the context of this disclosure, a number of terms shall be utilized. The terms "protein" and "polypeptide" are used interchangeably herein. Each protein or polypeptide has a unique function.

"Altered levels" or "altered expression" refers to the production of gene product(s) in transgenic organisms in amounts or proportions that differ from that of normal or non-transformed organisms.

"Null mutant" refers to a host cell which either lacks the expression of a certain polypeptide or expresses a polypeptide which is inactive or does not have any detectable expected enzymatic function.

"Mature protein" refers to a post-translationally processed polypeptide; i.e., one from which any pre- or propeptides present in the primary translation product have been removed. "Precursor protein" refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) Meth. Enzymol. 143:277) and particle-accelerated or "gene gun" transformation technology (Klein et al. (1987) *Nature* (London) 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is a technique used for the amplification of specific DNA segments (U.S. Pat. Nos. 4,683,195 and 4,800,159).

The present invention concerns an isolated polynucleotide comprising a nucleotide sequence selected from the group consisting of: (a) a first nucleotide sequence encoding a polypeptide of at least 30 amino acids having at least 85% identity based on the Clustal method of alignment when compared to a polypeptide of SEQ ID NO:6; (b) a second nucleotide sequence encoding a polypeptide of at least 50 amino acids having at least 80% identity based on the Clustal method of alignment when compared to a polypeptide selected from the group consisting of SEQ ID NOs:16, 28, 36, and 40; (c) a third nucleotide sequence encoding a polypeptide of at least 50 amino acids having at least 85% identity based on the Clustal method of alignment when compared to a polypeptide of SEQ ID NO:12; (d) a fourth nucleotide sequence encoding a polypeptide of at least 50 amino acids having at least 90% identity based on the Clustal method of alignment when compared to a polypeptide selected from the group consisting of SEQ ID NOs:8 and 24; (e) a fifth nucleotide sequence encoding a polypeptide of at least 50 amino acids having at least 95% identity based on the Clustal method of alignment when compared to a polypeptide selected from the group consisting of SEQ ID NOs:18 and 32; (f) a sixth nucleotide sequence encoding a polypeptide of at least 90 amino acids having at least 95% identity based on the Clustal method of alignment when compared to a polypeptide of SEQ ID NO:42; (g) a seventh nucleotide sequence encoding a polypeptide of at least 95 amino acids that has at least 95% identity based on the Clustal method of alignment when compared to a polypeptide of SEQ ID NO:46; (h) an eighth nucleotide sequence encoding a polypeptide of at least 100 amino acids having at least 80% identity based on the Clustal method of alignment when compared to a polypeptide selected from the group consisting of SEQ ID NO:20; (i) a ninth nucleotide sequence encoding a polypeptide of at least 100 amino acids having at least 90% identity based on the Clustal method of alignment when compared to a polypeptide of SEQ ID NO:2; (j) a tenth nucleotide sequence encoding a polypeptide of at least 150 amino acids having at least 95% identity based on the Clustal method of alignment when compared to a polypeptide of SEQ ID NO:4; (k) an eleventh nucleotide sequence encoding a polypeptide of at least 300 amino acids having at least 80% identity based on the Clustal method of alignment when compared to a polypeptide of SEQ ID NO:38; (l) a twelfth nucleotide sequence encoding a polypeptide of at least 350 amino acids having at least 95% identity based on the Clustal method of alignment when compared to a polypeptide of SEQ ID NO:10; (m) a thirteenth nucleotide sequence encoding a polypeptide of at least 400 amino acids having at least 80% identity based on the Clustal method of alignment when compared to a polypeptide selected from the group consisting of SEQ ID NOs:22, 26 and 30; (n) a fourteenth nucleotide sequence encoding a polypeptide of at least 500 amino acids having at least 80% identity based on the Clustal method of alignment when compared to a polypeptide of SEQ ID NO:34; (o) a fifteenth nucleotide sequence encoding a polypeptide of at least 200 amino acids having at least 80% identity based on the Clustal method of alignment when compared to a polypeptide of SEQ ID NO:14; (p) a sixteenth nucleotide sequence encoding a polypeptide of at least 250 amino acids having at least 90% identity based on the Clustal method of alignment when compared to a polypeptide of SEQ ID NO:48; and (q) a seventeenth nucleotide sequence comprising the complement of (a), (b), (c), (d), (e), (f), (g), (h), (i), (j), (k), (l), (m), (n), (o) or (p).

Preferably, the first nucleotide sequence comprises a nucleic acid sequence selected from the group consisting of SEQ ID NOs:1, 3, 5, 7, 9, 11, 13, 15, 17, 19, 21, 23, 25, 27, 29, 31, 33, 35, 37, 39, 41, 45, and 47 that codes for the polypeptide selected from the group consisting of SEQ ID NOs:2, 4, 6, 8, 10, 12, 14, 16, 18, 20, 22, 24, 26, 28, 30, 32, 34, 36, 38, 40, 42, 46, and 48.

Nucleic acid fragments encoding at least a substantial portion of several auxin transport proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other auxin transport polypeptides, either as cDNAs or genomic DNAs, could be isolated directly by using all or a substantial portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequence(s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 45, and 47 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of an auxin transport polypeptide, preferably a substantial portion of a plant auxin transport polypeptide, comprising the steps of synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, 41, 45, and 47 and the complement of such nucleotide sequences; and amplifying a nucleic acid fragment (preferably a cDNA inserted in a cloning vector) using the oligonucleotide primer. The amplified nucleic acid fragment preferably will encode a substantial portion of an auxin transport polypeptide.

Availability of the instant nucleotide and deduced amino acid sequences facilitates immunological screening of cDNA expression libraries. Synthetic peptides representing substantial portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of auxin efflux in those cells. In addition, since some of these auxin transport proteins may be root-specific and impact root development to a significant degree, these auxin transport proteins may lead to novel strategies for developing transgenic plants with more robust root systems, which may enhance food production, especially in arid climates. The nucleic acid fragments of the instant invention may also be used to regulate root angle, and thus modify plant susceptibility to root lodging, root angle being a determinant of lodging susceptibility. Modified root gravitropic responses (as mediated by manipulation of the nucleic acid fragments of the instant invention) would also be useful for redirecting root growth (by inhibiting gravitropism in short durations) for soil remediation projects and alleviate soil erosion problems. Roots may also be made to grow deeper beyond the top layers of the soil, reducing root tip damage caused by insect feeding and possibly generating a root system that extends downward rather than laterally into neighboring root zones, thus minimizing competition for nutrients among different root systems, making planting at higher densities a possibility. The auxin transport proteins disclosed herein may also be engineered to transport other compounds into and/or out of the plant, for example, such as into storage compartments or into media for harvesting.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns an auxin transport polypeptide selected from the group consisting of: (a) a polypeptide of at least 30 amino acids having at least 85% identity based on the Clustal method of alignment when compared to a polypeptide of SEQ ID NO:6; (b) a polypeptide of at least 50 amino acids having at least 80% identity based on the Clustal method of alignment when compared to a polypeptide selected from the group consisting of SEQ ID NOs:16, 28, 36, and 40; (c) a polypeptide of at least 50 amino acids having at least 85% identity based on the Clustal method of alignment when compared to a polypeptide of SEQ ID NO:12; (d) a polypeptide of at least 50 amino acids having at least 90% identity based on the Clustal method of alignment when compared to a polypeptide selected from the group consisting of SEQ ID NOs:8 and 24; (e) a polypeptide of at least 50 amino acids having at least 95% identity based on the Clustal method of alignment when compared to a polypeptide selected from the group consisting of SEQ ID NOs:18 and 32; (f) a polypeptide of at least 90 amino acids having at least 95% identity based on the Clustal method of alignment when compared to a polypeptide of SEQ ID NO:42; (g) a polypeptide of at least 95 amino acids having at least 95% identity based on the Clustal method of alignment when compared to a polypeptide of SEQ ID NO:46; (h) a polypeptide of at least 100 amino acids having at least 80% identity based on the Clustal method of alignment when compared to a polypeptide selected from the group consisting of SEQ ID NO:20; (i) a polypeptide of at least 100 amino acids having at least 90% identity based on the Clustal method of alignment when compared to a polypeptide of SEQ ID NO:2; (j) a polypeptide of at least 150 amino acids having at least 95% identity based on the Clustal method of alignment when compared to a polypeptide of SEQ ID NO:4; (k) a polypeptide of at least 300 amino acids having at least 80% identity based on the Clustal method of alignment when compared to a polypeptide of SEQ ID NO:38; (l) a polypeptide of at least 350 amino acids having at least 95% identity based on the Clustal method of alignment when compared to a polypeptide of SEQ ID NO:10; (m) a polypeptide of at least 400 amino acids having at least 80% identity based on the Clustal method of alignment when compared to a polypeptide selected from the group consisting of SEQ ID NOs:22, 26 and 30; (n) a polypeptide of at least 500 amino acids having at least 80% identity based on the Clustal method of alignment when compared to a polypeptide of SEQ ID NO:34; (o) a polypeptide of at least 200 amino acids having at least 80% identity based on the Clustal method of alignment when compared to a polypeptide of SEQ ID NO:14; (p) a polypeptide of at least 250 amino acids having at least 90% identity based on the Clustal method of alignment when compared to a polypeptide of SEQ ID NO:48.

The instant polypeptides (or portions thereof) may be produced in heterologous host cells, particularly in the cells of microbial hosts, and can be used to prepare antibodies to the proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded auxin transport protein. An example of a vector for high level expression of the instant polypeptides in a bacterial host is provided (Example 6).

Additionally, the instant auxin transport proteins can be used as a target to facilitate design and/or identification of inhibitors of these proteins that may be useful as herbicides. This is desirable because the auxin transport proteins described herein are essential components of the polar transport system involved in auxin redistribution and hence auxin function. Accordingly, inhibition of the activity of one or more of the enzymes described herein could lead to inhibition of plant growth. Thus, the instant auxin transport proteins could be appropriate for new herbicide discovery and design.

The present invention further provides a method for modulating (i.e., increasing or decreasing) the concentration or composition of the polypeptides of the present invention in a plant or part thereof. Modulation of the polypeptides can be effected by increasing or decreasing the concentration and/or the composition of the polypeptides in a plant. The method comprises transforming a plant cell with a construct comprising a nucleic acid fragment of the present invention to obtain a transformed plant cell, growing the transformed plant cell under plant forming conditions, and expressing the nucleic acid fragment in the plant for a time sufficient to modulate concentration and/or composition of the polypeptides in the plant or plant part.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868.

In some embodiments, an isolated nucleic acid fragment (e.g., a vector) comprising a promoter sequence is transfected into a plant cell. Subsequently, a plant cell comprising the isolated nucleic acid is selected for by means known to those of skill in the art such as, but not limited to, Southern blot, DNA sequencing, or PCR analysis using primers specific to the promoter and to the nucleic acid and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, concentration of the polypeptides is increased or decreased by at least 5%, 10%, 20%, 30%, 40%, 50%, 60%, 70%, 80%, or 90% relative to a native control plant, plant part, or cell lacking the aforementioned transgene. Modulation in the present invention may occur during and/or subsequent to growth of the plant to the desired stage of development.

Modulating nucleic acid expression temporally and/or in particular tissues can be controlled by employing the appropriate promoter operably linked to a nucleic acid fragment of the present invention in, for example, sense or antisense orientation as discussed in greater detail above. Induction of expression of a nucleic acid fragment of the present invention can also be controlled by exogenous administration of an effective amount of inducing compound. Inducible promoters and inducing compounds that activate expression from these promoters are well known in the art.

Examples of inducible promoters are the Adh1 promoter which is inducible by hypoxia or cold stress, the Hsp70 promoter which is inducible by heat stress, and the PPDK promoter which is inducible by light. Also useful are promoters which are chemically inducible.

Examples of promoters under developmental control include promoters that initiate transcription preferentially in certain tissues such as leaves, roots, fruit, seeds, or flowers. An exemplary promoter is the another specific promoter 5126 (U.S. Pat. Nos. 5,689,049 and 5,689,051). Examples of seed-preferred promoters include, but are not limited to, 27 kD gamma zein promoter and waxy promoter (Boronat et al. (1986) *Plant Sci.* 47:95-102; Reina et al. (1990) *Nucleic Acids Res.* 18(21):6426; Kloesgen et al. (1986) *Mol. Gen. Genet.* 203:237-244). Promoters that are expressed in the embryo, pericarp, and endosperm are disclosed in U.S. application Ser. Nos. 60/097,233 filed Aug. 20, 1998 and 60/098,230 filed Aug. 28, 1998. The disclosures of each of these are incorporated herein by reference in their entirety.

Either heterologous or non-heterologous (i.e., endogenous) promoters can be employed to direct expression of the nucleic acids of the present invention. These promoters can also be used, for example, in chimeric genes to drive expression of antisense nucleic acids to reduce, increase, or alter concentration and/or composition of the proteins of the present invention in a desired tissue.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as Map-Maker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci. USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor.

With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries: Isolation and Sequencing of cDNA Clones cDNA libraries representing mRNAs from various corn (*Zea mays*), rice (*Oryza sativa*), soybean (*Glycine max*), and wheat (*Triticum aestivum*) tissues were prepared. The characteristics of the libraries are described below. Corn developmental stages are explained in the publication "How a Corn Plant Develops" from the Iowa State University Coop. Ext. Service Special Report No. 48 reprinted June 1993.

TABLE 2 cDNA Libraries from Corn, Rice, Soybean, and Wheat

| Library | Tissue | Clone |
| --- | --- | --- |
| ceb1 | Corn Embryo 10 to 11 Days After Pollination | ceb1.pk0082.a5 |
| cil1c | Corn (EB90) Pooled Immature Leaf Tissue at V4, V6 and V8 | cil1c.pk001.b7 |
| cr1 | Corn Root From 7 Day Old Seedlings | cr1.pk0022.a4 |
| cr1n | Corn Root From 7 Day Old Seedlings* | cr1n.pk0033.e3 |
| csi1n | Corn Silk* | csi1n.pk0045.a5 |
|  |  | csi1n.pk0050.d5 |
| p0005 | Corn Immature Ear | p0005.cbmej72r |
| p0016 | Corn Tassel Shoot, Pooled, 0.1-1.4 cm | p0016.ctsag12r |
| p0041 | Corn Root Tip Smaller Than 5 mm in Length, Four Days After Imbibition | p0041.crtba02r |
| p0094 | Corn Leaf Collars for the Ear Leaf (EL), screened 1 and the Next Leaf Above and Below the EL; Growth Conditions: Field; Control or Untreated Tissues | p0094.csssh17r |
| p0097 | Corn V9 Whorl Section (7 cm) From Plant Infected Four Times With European Corn Borer | p0097.cqrai63r |
| p0119 | Corn V12-Stage Ear Shoot With Husk, Night Harvested* | p0119.cmtnl24r |
| rr1 | Rice Root of Two Week Old Developing Seedling | rr1.pk0019.c4 |
| rsl1n | Rice 15-Day-Old Seedling* | rsl1n.pk003.n3 |
| scr1c | Soybean Embryogenic Suspension Culture Subjected to 4 Vacuum Cycles and Collected 12 Hrs Later | scr1c.pk003.g7 |
| sdp4c | Soybean Developing Pod (10-12 mm) | sdp4c.pk003.h2 |
| sfl1 | Soybean Immature Flower | sfl1.pk131.g9 |
| src3c | Soybean 8 Day Old Root Infected With Cyst Nematode | src3c.pk026.o11 |
| wdk1c | Wheat Developing Kernel, 3 Days After Anthesis | wdk1c.pk008.g12 |
| wdr1f | Wheat Developing Root (Full Length) | wdr1f.pk001.g9 |
| wle1n | Wheat Leaf From 7 Day Old Etiolated Seedling* | wle1n.pk0109.h1 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Example 2

Identification of cDNA Clones cDNA clones encoding auxin transport protein were identified by conducting BLAST (Basic Local Alignment Search Tool; Altschul et al. (1993) *J. Mol. Biol.* 215:403-401 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (199) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Auxin Transport Protein

The BLASTX search using the EST sequences from clones p0016. ctsag12r, p0119. cmtn124r and wle1n.pk0109. h 1, and the contig assembled from EST sequences from clones p0097. cqrai63r and p0094. csssh17r revealed similarity of the proteins encoded by the cDNAs to the auxin transport protein encoded by REH1 (Rice EIR1 Homolog) from rice (NCBI Gene Identifier No. 3377509). The BLAST results for each of these ESTs are shown in Table 3:

TABLE 3

BLAST Results for Clones Encoding Polypeptides
Homologous to REH1 Protein

| Clone | BLAST pLog Score 3377509 |
|---|---|
| p0016.ctsag12r | 10.5 |
| Contig of: | 40.7 |
| p0097.cqrai63r | |
| p0094.csssh17r | |
| p0119.cmtnl24r | 34.4 |
| wle1n.pk0109.h1 | 52.0 |

The BLASTX search using the EST sequences from clones rsl1n.pk 003. n 3, src3c.pk026. o 11 and wdk1c.pk008. g 12 revealed similarity of the proteins encoded by the cDNAs to the auxin transport protein encoded by EIR1 from *Arabidopsis thaliana* (NCBI Gene Identifier No. 3377507). The BLAST results for each of these ESTs are shown in Table 4:

TABLE 4

BLAST Results for Clones Encoding Polypeptides
Homologous to EIR1 Protein

| Clone | BLAST pLog Score 3377507 |
|---|---|
| rsl1n.pk003.n3 | 38.2 |
| src3c.pk026.o11 | 39.2 |
| wdk1c.pk008.g12 | 41.0 |

The BLASTX search using the EST sequences from clone sfl1. pk 131. g 9 revealed similarity of the protein encoded by the cDNA to the auxin transport protein encoded by PIN1 from *Arabidopsis thaliana* (NCBI Gene Identifier No. 4151319) with a pLog value of 30.2. The BLASTX search using the EST sequences from clone sdp4c.pk003. h 2 revealed similarity of the protein encoded by the cDNA to a putative auxin transport protein encoded by a gene from *Arabidopsis thaliana* (NCBI Gene Identifier No. 3785972) with a pLog value of 37.7.

The sequence of a substantial portion of the cDNA insert from clone p0016. ctsag12r is shown in SEQ ID NO:5; the deduced amino acid sequence of this portion of the cDNA is shown in SEQ ID NO:6. The sequence of a contig assembled from a portion of the cDNA insert from clones p0097. cqrai63r and p0094. csssh17r is shown in SEQ ID NO:7; the deduced amino acid sequence of this contig is shown in SEQ ID NO:8. The sequence of a substantial portion of the cDNA insert from clone p0119. cmtn124r is shown in SEQ ID NO:11; the deduced amino acid sequence of this portion of the cDNA is shown in SEQ ID NO:12. The sequence of a substantial portion of the cDNA insert from clone rsl1n.pk003. n3 is shown in SEQ ID NO:17; the deduced amino acid sequence of this portion of the cDNA is shown in SEQ ID NO:18. The sequence of a substantial portion of the cDNA insert from clone sdp4c.pk003.112 is shown in SEQ ID NO:23; the deduced amino acid sequence of this portion of the cDNA is shown in SEQ ID NO:24. The sequence of a substantial portion of the cDNA insert from clone sfl1. pk131. g 9 is shown in SEQ ID NO:27; the deduced amino acid sequence of this portion of the cDNA is shown in SEQ ID NO:28. The sequence of a substantial portion of the cDNA insert from clone src3c.pk026. o 11 is shown in SEQ ID NO:31; the deduced amino acid sequence of this portion of the cDNA is shown in SEQ ID NO:32. The sequence of a substantial portion of the cDNA insert from clone wdk1c.pk008. 12 is shown in SEQ ID NO:35; the deduced amino acid sequenceof this portion of the cDNA is shown in SEQ ID NO:36. The sequence of a substantial portion of the cDNA insert from wle1n.pk0109. h1 is shown in SEQ ID NO:41; the deduced amino acid sequence of this cDNA is shown in SEQ ID NO:42. BLAST scores and probabilities indicate that the instant nucleic acid fragments encode portions of auxin transport proteins.

The BLASTX search using the EST sequences from clones listed in Table 5 revealed similarity of the polypeptides encoded by the cDNAs to auxin transport proteins from rice (NCBI GenBank Identifier (GI) Nos. 3377509 and 7489524) and *Arabidopsis* (NCBI GenBank Identifier (GI) Nos. 5902405, 5817301, 4151319, 3377507, and 3785972). Shown in Table 5 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 5

BLAST Results for Sequences Encoding Polypeptides
Homologous to Auxin Transport Protein

| | | BLAST Results | |
|---|---|---|---|
| Clone | Status | NCBI GenBank Identifier (GI) No. | pLog Score |
| ceb1.pk0082.a5 | EST | 3377509 | 79.10 |
| Contig of: | Contig | 3377509 | 91.70 |
| cr1.pk0022.a4 | | | |
| cr1n.pk0033.e3 | | | |
| csi1n.pk0045.a5 | | | |
| csi1n.pk0050.d5 | | | |
| p0005.cbmej72r | | | |
| p0041.crtba02r | | | |

TABLE 5-continued

BLAST Results for Sequences Encoding Polypeptides
Homologous to Auxin Transport Protein

| Clone | Status | NCBI GenBank Identifier (GI) No. | BLAST Results pLog Score |
|---|---|---|---|
| p0094.csssh17r | FIS | 3377509 | >254.00 |
| p0119.cmtnl24r (FIS) | CGS | 7489524 | 180.00 |
| cil1.pk001.b7 | FIS | 7489524 | 135.00 |
| rr1.pk0019.c4 | EST | 5902405 | 33.30 |
| rsl1n.pk003.n3 | FIS | 5817301 | 155.00 |
| scr1c.pk003.g7 | FIS | 4151319 | 170.00 |
| sdp4c.pk003.h2 | FIS | 5817301 | >254.00 |
| sfl1.pk131.g9(FIS) | CGS | 4151319 | >254.00 |
| src3c.pk026.o11(FIS) | CGS | 3377507 | >254.00 |
| wdk1c.pk008.g12(FIS) | CGS | 3377507 | >254.00 |
| wdr1f.pk001.g9 | EST | 3785972 | 27.30 |
| wle1n.pko109.h1 | FIS | 3377509 | 48.00 |

FIG. 1 presents an alignment of the amino acid sequences set forth in SEQ ID NOs:14, 30, 34, and 38, the auxin transport protein EIR1 sequence from *Arabidopsis thaliana* (NCBI GenBank Identifier (GI) No. 3377507; SEQ ID NO:43), and the auxin transport protein AtPIN1 sequence from *Arabidopsis thaliana* (NCBI GenBank Identifier (GI) No. 4151319; SEQ ID NO:44). The data in Table 6 represents a calculation of the percent identity of the amino acid sequences set forth in SEQ ID NOs:14, 30, 34, and 38, the auxin transport protein EIR1 sequence from *Arabidopsis thaliana* (NCBI GenBank Identifier (GI) No. 3377507; SEQ ID NO:43), and the auxin transport protein AtPIN1 from *Arabidopsis thaliana* (NCBI GenBank Identifier (GD No. 4151319; SEQ ID NO:44).

TABLE 6

Percent Identity of Amino Acid Sequences Deduced From
the Nucleotide Sequences of cDNA Clones Encoding Polypeptides
Homologous to Auxin Transport Protein

| SEQ ID NO. | Percent Identity to | |
|---|---|---|
| | SEQ ID NO: 43 | SEQ ID NO: 44 |
| 14 | 51.5 | 55.3 |
| 30 | 57.9 | 72.3 |
| 34 | 75.1 | 59.6 |
| 38 | 59.7 | 52.1 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the nucleic acid fragments comprising the instant cDNA clones encode all or a substantial portion of an auxin transport protein.

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μl, of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 5

Expression of Chimeric Genes in Dicot Cells

A seed-specific construct composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed construct comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μl of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 4 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTGT™ low melting agarose gel (FMC). Buffer and agarose contain 10 μg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Evaluating Compounds for their Ability to Inhibit the Activity of Auxin Transport Proteins The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the auxin transport proteins disclosed herein. Assays may be conducted under well known experimental conditions which permit optimal enzymatic activity. For example, assays for auxin transport proteins are presented by Chen, R. et al., (1998) *Proc. Natl. Acad. Sci. USA* 95:15112-15117.

What is claimed is:

1. An isolated polynucleotide comprising a nucleotide sequence encoding a polypeptide having auxin transport activity, wherein
said nucleotide sequence comprises SEQ ID NO:37.

* * * * *